(12) United States Patent
Van Amerongen et al.

(10) Patent No.: US 6,605,698 B1
(45) Date of Patent: Aug. 12, 2003

(54) ANTIFUNGAL PEPTIDES AND COMPOSITION THEREOF

(75) Inventors: Aart Van Amerongen, Veenendaal (NL); Franky Fant, Wetteren (BE); Frans Alois Borremans, Destelbergen (BE); Genoveva Wivina De Samblanx, Heverlee (BE); Lolke Sijtsma, Renkum (NL); Robbert Hans Meloen, Lelystad (NL); Wouter Cornelis Puijk, Lelystad (NL); Wilhelmus Martinus Maria Schaaper, Almere (NL); Willem Frans Broekaert, Dilbeek (BE); Wilhelmus Martinus Josef van Gelder, Zoetermeer (NL); Sarah Bronwen Rees, Bracknell (GB)

(73) Assignee: Syngenta Limited, Guildford (GB)

(*) Notice: Subject to any disclaimer, the term of this patent is extended or adjusted under 35 U.S.C. 154(b) by 0 days.

(21) Appl. No.: 09/077,948

(22) PCT Filed: Dec. 12, 1996

(86) PCT No.: PCT/GB96/03068

§ 371 (c)(1),
(2), (4) Date: Aug. 7, 1998

(87) PCT Pub. No.: WO97/21815

PCT Pub. Date: Jun. 19, 1997

(30) Foreign Application Priority Data

Dec. 13, 1995 (GB) .................................. 9525455
Mar. 28, 1996 (GB) .................................. 9606552

(51) Int. Cl.[7] ............................................. C07K 1/00
(52) U.S. Cl. ................... 530/350; 530/300; 435/430; 435/69.1; 435/252.3; 435/252.33; 435/320.1; 435/410; 435/419; 800/294; 800/278; 800/280; 800/281; 800/290; 536/23.6; 536/24.3
(58) Field of Search .................. 530/350, 300; 800/294, 278, 280, 281, 290; 536/23.6, 24.3; 435/430, 69.1, 252.3, 252.33, 320.1, 410, 419

(56) References Cited

FOREIGN PATENT DOCUMENTS

| | | |
|---|---|---|
| WO | WO 87/03303 | 6/1987 |
| WO | WO 90/13224 | 11/1990 |
| WO | WO 91/10363 | 7/1991 |
| WO | WO 93/05153 | 3/1993 |
| WO | WO 94/16076 | 7/1994 |
| WO | WO 95/18229 | 7/1995 |
| WO | WO 95/24486 | 9/1995 |

OTHER PUBLICATIONS

Alignments.*
Terras, F.R.G. et al., "Analysis of Two Novel Classes of Plant Antifungal Proteins from Radish (*Raphanus sativus* L) Seeds", Journal of Biological Chemistry, vol. 267, p. 15301–15309, 1992.
Terras, F.R.G. et al., "Small Cysteine–Rich Antifungal Proteins from Radish: Their Role in Host Defense", The Plant Cell, vol. 7, p. 573–588, 1995.1.
Broekaert, W.F. et al., "Plant .Defensin: Novel Antimicrobial Peptides as Components of the Host Defense System", Plant Physiol, vol. 108, p. 1353–1358, 1995.
Terras, F.R.G. et al., "A new family of basis cysteine–rich plant antifungal proteins from Brassicaceae species", FEBS Letters, vol. 316, No. 3, p. 233–240, 1993.
Broekaert. W.F. et al., "An automated quantitative assay for fungal growth inhibition", FEMS Microbiology Letters, vol. 69, p. 55–60, 1990.
Osborn, R.W. et al., "Isolation and characterisation of plant defensins from seeds of Asteraceae, Fabaceae, Hippocastanaceae and Saxifragaceae", FEBS Letters, vol. 368, No. 2, p. 257–262, 1995.
Rees, S.B. et al., "Plant antifungal proteins: novel crop protection agents", in G.K. Dixon et al. editors, *Antifungal Agents: Discovery Mode Action*, Bios Scientific Publishers, Oxford, United Kingdom, chap. 16, p. 193–200, 1995.
De Samblanx, G.W. et al., "Antifungal Activity of Synthetic 15–mer Peptides Based on the Rs–AFP2 (*Raphanus sativus* antifungal protein 2) Sequence", Peptide Research, vol. 9, No. 6, p. 262–268, 1996.
Cammue, B.P.A. et al., "Gene–encoded antimicrobial peptides from plants", CIBA Foundation Symp. No. 186, p 91–106, 1994.
Vilas Alves, A.L. et al., "Expression of functional *Raphanus sativus* antifungal protein in yeast", FEBS Letters, vol. 348, p. 228–232, 1994.
Mor, A. et al., "The Vertebrate Peptide Antibiotices Dermaseptins Have Overlapping Structural Features but Target Specific Microorganisms", The Journal of Biol. Chemistry, vol. 269, No. 50, p. 31635–31641, 1994.

* cited by examiner

*Primary Examiner*—Christopher S. F. Low
*Assistant Examiner*—Hope A. Robinson
(74) *Attorney, Agent, or Firm*—Hale & Dorr; Syngenta Limited

(57) ABSTRACT

Antifungal peptides which comprise at least six amino acid residues identical to a run of amino acid residues found between position 21 and position 51 of the Rs-AFP2 antifungal protein sequence or of substantially homologous protein sequences. The peptides are useful for combating fungal diseases in agricultural, pharmaceutical or preservative applications.

8 Claims, 23 Drawing Sheets

|          | 1           | 11          | 21          | 31         | 41         | 51 |
|----------|-------------|-------------|-------------|------------|------------|----|
| Rs-AFP1  | QKLCERPSGT  | WSGVCGNNNA  | CKNQCINLEK  | ARHGSCNYVF | PAHKCICYFP | C  |
| Rs-AFP2  | QKLCQRPSGT  | WSGVCGNNNA  | CKNQCIRLEK  | ARHGSCNYVF | PAHKCICYFP | C  |
| Rs-AFP3  | -KLCERSSGT  | WSGVCGNNNA  | CKNQCIRLEG  | AQHGSCNYVF | PAHKCICYFP | C  |
| Rs-AFP4  | QKLCERSSGT  | WSGVCGNNNA  | CKNQCINLEG  | ARHGSCNYIF | PYHRCICYFP | C  |
| Br-AFP1  | QKLCERPSGT  | WSGVCGNNNA  | CKNQCIN     |            |            |    |
| Br-AFP2  | QKLCERPSGT  | ?SGVCGNNNA  | CKNQCIR     |            |            |    |
| Bn-AFP1  | QKLCERPSGT  | WSGVCGNNNA  | CKNQCINLEK  |            |            |    |
| Bn-AFP2  | QKLCERPSGT  | WSGVCGNNNA  | CKN         |            |            |    |
| Sa-AFP1  | QKLCERPSGT  | WSGVCGNNNA  | CKNQC       |            |            |    |
| Sa-AFP2  | QKLCQRPSGT  | WSGVCGNNNA  | CRNQCI      |            |            |    |
| At-AFP1  | QKLCERPSGT  | WSGVCGNSNA  | CKNQCIN     |            |            |    |

FIG. 1

```
GTTTATTAGTGATCATGGCTAAGTTTGCGTCCATCATCGCACTT           45
                 M   A   K   F   A   S   I   I   A   L
CTTTTTGCTGCTCTTGTTCTTTTTGCTGCTTTCGAAGCACCAACA           90
 L   F   A   A   L   V   L   F   A   A   F   E   A   E   T
ATGGTGGAAGCACAGAAGTTGTGCGAAAGGCCAAGTGGGACATGG          135
 M   V   E   A  |Q   K   L   C   E   R   P   S   G   T   W|
TCAGGAGTCTGTGGAAACAATAACGCATGCAAGAATCAGTGCATT          180
|S   G   V   C   G   N   N   N   A   C   K   N   Q   C   I|
AACCTTGAGAAAGCACGACACATGGATCTTGCAACTATGTCTTCCCA        225
|N   L   E   K   A   R   H   G   S   C   N   Y   V   F   P|
GCTCACAAGTGTATCTGCTACTTTCCCTTGTTAATTTATCGCAAAC         270
|A   H   K   C   I   C   Y   F   P   C|  *
TCTTTGGTGAATAGTTTTTATGTAATTTACACAAAATAAGTCAGT          315
GTCACTATCCATGAGTGATTTAAGACATGTACCAGATATGTTAT           360
GTTGGTTCGGTTATACAAATAAAGTTTTATTCACCAAAAAAAA            405
AAAAAAAAA                                              414
```

FIG. 2

```
              1          11          21          31          41         51
Rs-AFP2    QKLCQRPSGTWSGVCGNNNACKNQCIRLEKARHGSCNYVFPAHKCICYFPC

PEPTIDE 1  QKLCQRPSGTWSGVC
PEPTIDE 2   QRPSGTWSGVCGNNN
PEPTIDE 3      GTWSGVCGNNNACKN
PEPTIDE 4        GVCGNNNACKNQCIR
PEPTIDE 5            NNNACKNQCIRLEKA
PEPTIDE 6              CKNQCIRLEKARHGS
PEPTIDE 7                 CIRLEKARHGSCNYV
PEPTIDE 8                    EKARHGSCNYVFPAH
PEPTIDE 9                       HGSCNYVFPAHKCIC
PEPTIDE 10                        NYVFPAHKCICYFPC
```

FIG. 3

```
              1          11         21         31         41         51
Hs-AFP1   DGVKLCDVPSGTWSGHCGSSSKCSQQCKDREHFAYGGACHYQFPSVKCFCKRQC 1          11         21         31         41
Ah-AMP1   LCNERPSQTWSGNCGNTAHCDKQCQDWEKASHGACHKRENHWKCFCYFNC 1          11         21         31         41
Dm-AMP1   ELCEKASKTWSGNCGNTGHCDNQCKSWEGAAHGACHVRNGKHMCFCYFNC
```

FIG. 9

B = ALPHA-AMINOBUTYRIC ACID

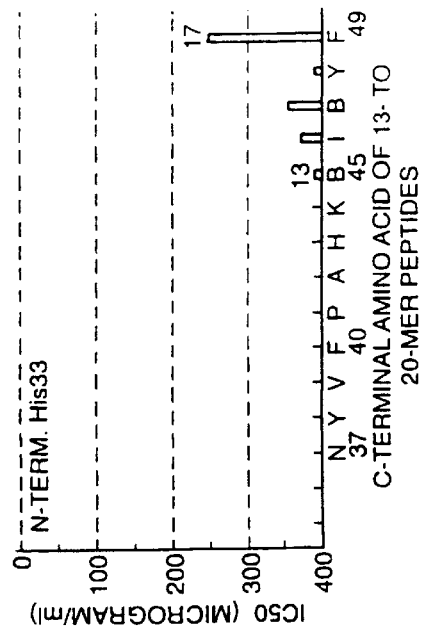
FIG. 11B-2
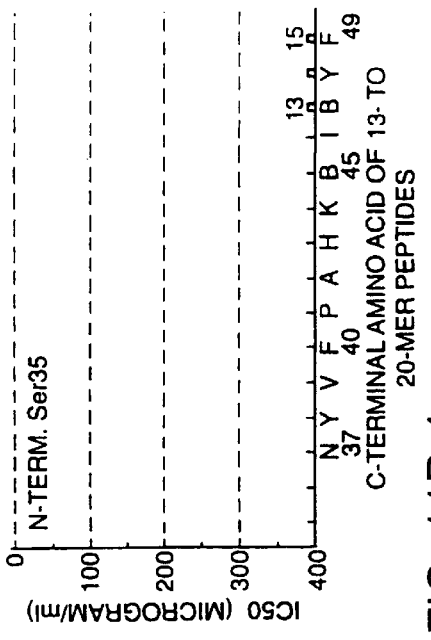
FIG. 11B-4
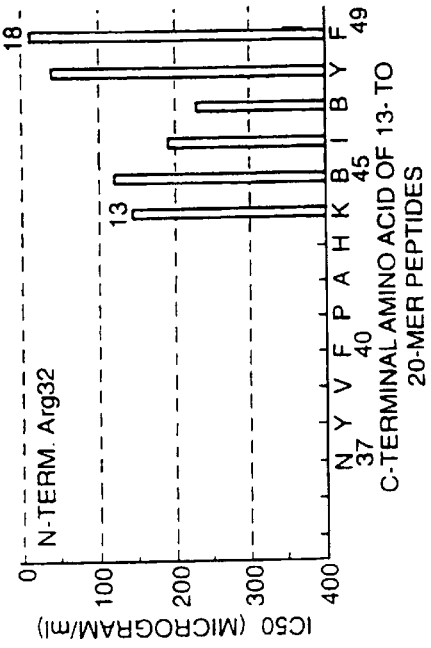
FIG. 11B-1
FIG. 11B-3

B = ALPHA-AMINOBUTYRIC ACID

B = ALPHA-AMINOBUTYRIC ACID

LOW ACTIVITY (13-20MERS)

His33 => Phe49    LOW ACTIVITY
    Ile26 <= Val39    LOW ACTIVITY

```
I R L E K A R H G S I N Y V F P A H K I I I Y F
26        30        35        40        45       49
```

GOOD/HIGH ACTIVITY

| | | |
|---|---|---|
| 13-MER | Arg32 + Lys44 | GOOD ACTIVITY |
| 14-MER | Arg27 + Phe40 | GOOD ACTIVITY |
| 14-MER | Lys30 + His43 | GOOD ACTIVITY |
| 17-MER | Arg32 + Tyr48 | VERY GOOD ACTIVITY |
| 17-MER | His33 + Phe49 | MODERATE ACTIVITY |
| 18-MER | Arg32 + Phe49 | VERY GOOD ACTIVITY |
| 19-MER | Ala31 + Phe49 | VERY GOOD ACTIVITY |
| 20-MER | Lys30 + Phe49 | HIGHEST ACTIVITY |

```
I R L E K A R H G S I N Y V F P A H K I I I Y F
26        30        35        40        45       49
```

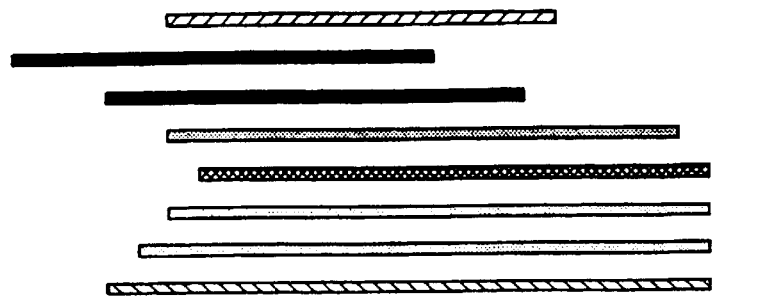

IC50 VALUES (µg/ml):

ANTIFUNGAL PEPTIDES AND COMPOSITION THEREOF

This application is a 371 of PCT/GB96/03068, filed Dec. 12, 1996 and claims prior to foreign application numbers UK/9525455.3, filed Dec. 13, 1995 and UK/9606552.9, filed Mar. 28, 1996.

This invention relates to antifungal proteins, processes for their manufacture and use, and DNA sequences encoding them.

In this context, antifungal proteins are defined as proteins or peptides possessing antifungal activity. Activity includes a range of antagonistic effects such as partial inhibition or death.

A wide range of antifungal proteins with activity against plant pathogenic fungi have been isolated from certain plant species. We have previously described a class of antifungal proteins capable of isolation from radish and other plant species. These proteins are described in the following publications which are specifically incorporated herein by reference: International Patent Application Publication Number W093/05153 published Mar. 18, 1993; Terras FRG et al, 1992, J Biol Chem, 267:15301–15309; Terras et al, 1993, FEBS Lett, 316:233–240; Terras et al, 1995, Plant Cell, 7:573–588. The class includes Rs-AFP1 (antifungal protein 1), Rs-AFP2, Rs-AFP3 and Rs-AFP4 from *Raphanus sativus* and homologous proteins such as Bn-AFP1 and Bn-AFP2 from *Brassica napus*, Br-AFP1 and Br-AFP2 from *Brassica rapa*, Sa-AFP1 and Sa-AFP2 from *Sinapis alba*, At-AFP1 from *Arabidopsis thaliana*, Dm-AMP1 and Dm-AMP2 from *Dahlia merckii*, Cb-AMP1 and Cb-AMP2 from *Cnicus benedictus*, Lc-AFP from *Lathyrus cicera*, Ct-AMP1 and Ct-AMP2 from *Clitoria ternatea*. The proteins specifically inhibit a range of fungi and may be used as fungicides for agricultural or pharmaceutical or preservative purposes.

It has been proposed that this class of antifungal proteins should be named plant defensins (Terras F.R.G. et al 1995, Plant Cell, 7 573–583) and these proteins have in common a similar motif of conserved cysteines and glycines (Broekaert W. F. et al 1995, Plant Physiol. 108 1353–1358).

FIG. 1 shows the amino acid sequences of the protein Rs-AFP1 (SEQ ID NO: 34) and the substantially homologous proteins Rs-AFP2 (SEQ ID NO: 35), Rs-AFP3 (SEQ ID NO: 36), Rs-AFP4 (SEQ ID NO: 37), Br-AFP1 (SEQ ID NO: 38), Br-AFP2 (SEQ ID NO: 39), Bn-AFP1 (SEQ ID NO: 40), Bn-AFP2 (SEQ ID NO: 41), Sa-AFP1 (SEQ ID NO: 42), Sa-AFP2 (SEQ ID NO: 43) and At-AFP1 (SEQ ID NO: 44) which are small 5 kDa polypeptides that are highly basic and rich in cysteine. FIG. 1 numbers the positions of the amino acid residues: the dash (-) at the start of the Rs-AFP3 (SEQ ID NO: 36) sequence indicates a gap introduced for maximum alignment. The sequences shown for Br-AFP1 (SEQ ID NO: 38), Br-AFP2 (SEQ ID NO: 39), Bn-AFP1 (SEQ ID NO: 40), Bn-AFP2 (SEQ ID NO: 41), Sa-AFP1 (SEQ ID NO: 42), Sa-AFP2 (SEQ ID NO: 43) and At-AFP1 (SEQ ID NO: 44) are not complete: only the N-terminal sequences are shown. The question mark (?) in the Br-AFP2 (SEQ ID NO: 39) sequence indicates a non-standard amino acid which the sequencing could not assign and which is thought to be a post-translational modification on one of the standard amino acid residues.

Further examples of antifungal plant defensins are described in International Patent Application Publication Number W095/18229 published Jul. 6, 1995 which is specifically incorporated herein by reference. These examples include Hs-AFP1, an antifungal protein capable of isolation from seeds of *Heuchera* species and Ah-AMP1, an antimicrobial protein capable of isolation from seeds of *Aesculus hippocastanum*. The proteins specifically inhibit a range of fungi and may be used as fungicides for agricultural or pharmaceutical or preservative purposes.

FIG. 9 shows the amino acid sequences of the proteins Hs-AFP1 and Ah-AMP1. FIG. 9 numbers the positions of the amino acid residues. The Hs-AFP1 sequence shows 48% sequence identity with Rs-AFP1. The Ah-AMP1 sequence shows 54% sequence identity with Rs-AFP1. Hs-AFP1 shows 52% identity to Ah-AMP1 on the amino acid sequence level.

The primary structures of the two antifungal protein isoforms capable of isolation from radish seeds, Rs-AFP1 and Rs-AFP2, only differ at two positions: the glutamic acid residue (E) at position 5 in Rs-AFP1 is a glutamine residue (Q) in Rs-AFP2, and the asparagine residue (N) at position 27 in Rs-AFP1 is substituted by an arginine residue (R) in Rs-AFP2. As a result, Rs-AFP2 has a higher net positive charge (+2) at physiological pH. Although both Rs-AFPs are 94% identical at the amino acid sequence level, Rs-AFP2 is two- to thirty-fold more active than Rs-AFP1on various fungi and shows an increased salt-tolerence. The proteins Rs-AFP3 and Rs-AFP4 are found in radish leaves following localized fungal infection. The induced leaf proteins are homologous to Rs-AFP1 and Rs-AFP2 and exert similar antifungal activity in vitro.

The cDNA encoding Rs-AFP1 encodes a preprotein with a signal peptide followed by the mature protein. The cDNA sequence is shown in FIG. 2. *Saccharomyces cerevisiae* can be used as a vector for the production and secretion of Rs-AFP2 (Vilas Alves et al, FEBS Lett, 1994, 348:228–232). Plant-derivable "wild-type" Rs-AFP2 can be correctly processed and secreted by yeast when expressed as a N-terminal fusion to the yeast mating factor α1 (MFα1) preprosequence. The Rs-AFP2 protein does not have adverse effects on yeast even at concentrations as high as 500 μg/ml.

We now provide new potent antifungal peptides based on the structure of the Rs-AFPs and related plant defensins.

According to the first aspect of the present invention there is provided an antifungal peptide which comprises at least six amino acid residues identical to a run of amino acid residues found between position 21 and position 51 of the Rs-AFP2 sequence shown in FIG. 1 or of substantially homologous protein sequences.

Proteins which are substantially homologous to the Rs-AFP2 protein include the proteins Rs-AFP1, Rs-AFP3, Rs-AFP4, Br-AFP1, Br-AFP2, Bn-AFP1, Bn-AFP2, Sa-AFP1, Sa-AFP2 and At-AFP1 shown in FIG. 1 and Hs-AFP2, Ah-AMP1 and Dm-AMP1 shown in FIG. 9. Proteins which are substantially homologous have an amino acid sequence with at least 40% sequence identity to any of the sequences shown in FIGS. 1 and 9, and preferably at least 60% identity; and most preferably at least 80% identity.

Antifungal peptides according to the invention include especially peptides derived from the beta-2 strand/turn/beta-3 strand region of Rs-AFP2 and substantially homologous antifungal protein sequences. Preferred antifungal peptides according to the invention include the 6-mer, 9-mer and 12-mer, 13-mer, 14-mer, 15-mer, 16-mer, 17-mer, 18-mer, 19-mer and 20-mer, and most especially the 18-mer, 19-mer and 20-mer peptides described in the accompanying examples, figures and tables especially Example 11 and FIGS. 10 to 13.

Antifungal peptides according to the invention include the following peptides:

a peptide comprising fifteen amino acid residues identical to a run of fifteen amino acid residues found between position 21 and position 35 of the Rs-AFP2 sequence shown in FIG. 1 and having the sequence: CKNQCIR-LEKARHGS;

a peptide comprising fifteen amino acid residues identical to a run of fifteen amino acid residues found between position 25 and position 39 of the Rs-AFP2 sequence shown in FIG. 1 and having the sequence: CIRLE-KARHGSCNYV;

a peptide comprising fifteen amino acid residues identical to a run of fifteen amino acid residues found between position 29 and position 43 of the Rs-AFP2 sequence shown in FIG. 1 and having the sequence: EKARHG-SCNYVFPAH;

a peptide comprising fifteen amino acid residues identical to a run of fifteen amino acid residues found between position 33 and position 47 of the Rs-AFP2 sequence shown in FIG. 1 and having the sequence: HGSCNYVFPAHKCIC;

a peptide comprising ten amino acid residues identical to a run of ten amino acid residues found between position 36 and position 45 of the Rs-AFP2 sequence shown in FIG. 1 and having the sequence: CNYVFPAHKC;

a peptide comprising six amino acid residues identical to a run of six amino acid residues found between position 40 and position 45 of the Rs-AFP2 sequence shown in FIG. 1 and having the sequence: FPAHKC;

a peptide comprising six amino acid residues identical to a run of six amino acid residues found between position 42 and position 47 of the Rs-AFP2 sequence shown in FIG. 1 and having the sequence: AHKCIC;

a peptide comprising six amino acid residues identical to a run of six amino acid residues found between position 43 and position 48 of the Rs-AFP2 sequence shown in FIG. 1 and having the sequence: HKCICY;

a peptide comprising nine amino acid residues identical to a run of nine amino acid residues found between position 24 and position 32 of the Rs-AFP2 sequence shown in FIG. 1 and having the sequence: QCIRLE-KAR;

a peptide comprising nine amino acid residues identical to a run of nine amino acid residues found between position 25 and position 33 of the Rs-AFP2 sequence shown in FIG. 1 and having the sequence: CIRLE-KARH;

a peptide comprising nine amino acid residues identical to a run of nine amino acid residues found between position 32 and position 40 of the Rs-AFP2 sequence shown in FIG. 1 and having the sequence: RHG-SCNYVF;

a peptide comprising nine amino acid residues identical to a run of nine amino acid residues found between position 36 and position 44 of the Rs-AFP2 sequence shown in FIG. 1 and having the sequence: CNYVF-PAHK;

a peptide comprising nine amino acid residues identical to a run of nine amino acid residues found between position 40 and position 48 of the Rs-AFP2 sequence shown in FIG. 1 and having the sequence: FPAH-KCICY;

a peptide comprising nine amino acid residues identical to a run of nine amino acid residues found between position 41 and position 49 of the Rs-AFP2 sequence shown in FIG. 1 and having the sequence: PAHKCI-CYF;

a peptide comprising nine amino acid residues identical to a run of nine amino acid residues found between position 42 and position 50 of the Rs-AFP2 sequence shown in FIG. 1 and having the sequence: AHKCI-CYFP;

a peptide comprising nine amino acid residues identical to a run of nine amino acid residues found between position 43 and position 51 of the Rs-AFP2 sequence shown in FIG. 1 and having the sequence: HKCICY-FPC;

a peptide comprising twelve amino acid residues identical to a run of twelve amino acid residues found between position 25 and position 36 of the Rs-AFP2 sequence shown in FIG. 1 and having the sequence: CIRLE-KARHGSC;

a peptide comprising twelve amino acid residues identical to a run of twelve amino acid residues found between position 29 and position 40 of the Rs-AFP2 sequence shown in FIG. 1 and having the sequence: EKARHG-SCNYVF;

a peptide comprising twelve amino acid residues identical to a run of twelve amino acid residues found between position 30 and position 41 of the Rs-AFP2 sequence shown in FIG. 1 and having the sequence: KARHG-SCNYVFP;

a peptide comprising twelve amino acid residues identical to a run of twelve amino acid residues found between position 32 and position 43 of the Rs-AFP2 sequence shown in FIG. 1 and having the sequence: RHG-SCNYVFPAH;

a peptide comprising twelve amino acid residues identical to a run of twelve amino acid residues found between position 33 and position 44 of the Rs-AFP2 sequence shown in FIG. 1 and having the sequence: HGSCNYVFPAHK;

a peptide comprising nineteen amino acid residues identical to a run of nineteen amino acid residues found between position 31 and position 49 of the Rs-AFP2 sequence shown in FIG. 1 and having the sequence: ARHGSCNYVFPAHKCICYF.

We have found that the presence of an arginine residue at position 27 and a phenylalanine residue at position 40; a lysine residue at position 30 and a histidine residue at position 43 or an arginine residue at position 32 and a lysine residue at position 44 is particularly advantageous in Rs-AFP2 based peptides. We have also found that antifungal peptides based on the Rs-AFP2 sequence with an N-terminal amino acid selected from the group lysine at position 30, alanine at position 31, arginine at position 32 or histidine at position 33 and a C-terminal amino acid comprising either a tyrosine residue at position 48 or a phenylalanine residue at position 49 are particularly active. These antifungal peptides form a further embodiment of the invention.

The invention also provides an antifungal peptide which comprises at least six amino acid residues identical to a run of amino acid residues found between position 30 and position 48 of the Ah-AMP1 sequence or the Hs-AFP1 sequence shown in FIG. 9. Such antifungal peptides include a peptide comprising nineteen amino acid residues identical to the run of nineteen amino acid residues found between position 30 and position 48 of the Ah-AMP1 sequence shown in FIG. 9 and having the sequence: ASHGACH-KRENHWKCFCYF. The invention also provides a peptide comprising nineteen amino acid residues found between position 30 and position 48 of the Dm-AMP1 sequence shown in FIG. 9 and having the sequence AAHGACH-VRNGKHMCFCYF.

Peptides derived from the regions defined herein of the Rs-AFP plant defensins exhibit antifungal activity. Such peptides may be easier to synthesise than the full length plant defensin while retaining antifungal activity. DNA sequences encoding the peptides may also be more suitable for transformation into biological hosts.

An antifungal peptide according to the invention may be manufactured from its known amino acid sequence by chemical synthesis using a standard peptide synthesiser, or produced within a suitable organism (for example, a micro-organism or plant) by expression of recombinant DNA. The antifungal peptide is useful as a fungicide and may be used for agricultural or pharmaceutical or other applications. The antifungal peptide may be used in combination with one or more of the antifungal proteins or with one or more other antifungal peptides of the present invention. For example, an antifungal composition comprising one of the above-mentioned fifteen-mer peptides plus the Rs-AFP2 or Rs-AFP1 protein may show enhanced activity.

Knowledge of its primary structure enables manufacture of the antifungal peptide, or parts thereof, by chemical synthesis using a standard peptide synthesiser. It also enables production of DNA constructs encoding the antifungal peptide.

The invention further provides a DNA sequence encoding an antifungal peptide according to the invention. The DNA sequence may be predicted from the known amino acid sequence and DNA encoding the peptide may be manufactured using a standard nucleic acid synthesiser.

The DNA sequence encoding the antifungal peptide may be incorporated into a DNA construct or vector in combination with suitable regulatory sequences (promoter, terminator, transit peptide, etc). For some applications, the DNA sequence encoding the antifungal peptide may be inserted within a coding region expressing another protein to form an antifungal fusion protein or may be used to replace a domain of a protein to give that protein antifungal activity. The DNA sequence may be placed under the control of a homologous or heterologous promoter which may be a constitutive or an inducible promoter (stimulated by, for example, environmental conditions, presence of a pathogen, presence of a chemical). The transit peptide may be homologous or heterologous to the antifungal protein and will be chosen to ensure secretion to the desired organelle or to the extracellular space. The transit peptide is preferably that naturally associated with the antifungal protein of interest. Such a DNA construct may be cloned or transformed into a biological system which allows expression of the encoded peptide or an active part of the peptide. Suitable biological systems include micro-organisms (for example, bacteria such as *Escherichia coli*, Pseudomonas and endophytes such as *Clavibacter xyli* subsp. *cynodontis* (Cxc); yeast; viruses; bacteriophages; etc), cultured cells (such as insect cells, mammalian cells) and plants. In some cases, the expressed peptide may subsequently be extracted and isolated for use.

An antifungal peptide according to the invention is useful for combatting fungal diseases in plants. The invention further provides a process of combating fungi whereby they are exposed to an antifungal peptide according to the invention. The antifungal peptide may be used in the form of a composition.

For pharmaceutical applications, the antifungal peptide (including any product derived from it) may be used as a fungicide to treat mammalian infections (for example, to combat yeasts such as *Candida*).

An antifungal peptide (including any product derived from it) according to the invention may also be used as a preservative (for example, as a food additive).

For agricultural applications, the antifungal peptide may be used to improve the disease-resistance or disease-tolerance of crops either during the life of the plant or for post-harvest crop protection. Pathogens exposed to the peptides are inhibited. The antifungal peptide may eradicate a pathogen already established on the plant or may protect the plant from future pathogen attack. The eradicant effect of the peptide is particularly advantageous.

Exposure of a plant pathogen to an antifungal peptide may be achieved in various ways, for example:

(a) The isolated peptide may be applied to plant parts or to the soil or other growth medium surrounding the roots of the plants or to the seed of the plant before it is sown using standard agricultural techniques (such as spraying).

The peptide may have been extracted from plant tissue or chemically synthesised or extracted from micro-organisms genetically modified to express the peptide. The peptide may be applied to plants or to the plant growth medium in the form of a composition comprising the peptide in admixture with a solid or liquid diluent and optionally various adjuvants such as surface-active agents. Solid compositions may be in the form of dispersible powders, granules, or grains.

(b) A composition comprising a micro-organism genetically modified to express the antifungal peptide may be applied to a plant or the soil in which a plant grows.

(c) An endophyte genetically modified to express the antifungal peptide may be introduced into the plant tissue (for example, via a seed treatment process).

An endophyte is defined as a micro-organism having the ability to enter into non-pathogenic endosymbiotic relationships with a plant host. A method of endophyte-enhanced protection of plants has been described in a series of patent applications by Crop Genetics International Corporation (for example, International Application Publication Number WO90/13224, European Patent Publication Number EP-125468-B1, International Application Publication Number WO91/10363, International Application Publication Number WO87/03303). The endophyte may be genetically modified to produce agricultural chemicals. International Patent Application Publication Number WO94/16076 (ZENECA Limited) describes the use of endophytes which have been genetically modified to express a plant-derived antifungal peptide.

(d) DNA encoding an antifungal peptide may be introduced into the plant genome so that the peptide is expressed within the plant body (the DNA may be cDNA, genomic DNA or DNA manufactured using a standard nucleic acid synthesiser).

Exposure of a plant pathogen to an antifungal composition comprising an antifungal peptide plus an antifungal protein may be achieved by delivering the protein as well as the peptide as described above. For example, both one of the above-mentioned fifteen-mer peptides plus Rs-AFP2 or Rs-AFP1 could be simultaneously applied to plant parts or simultaneously expressed within the plant body.

Plant cells may be transformed with recombinant DNA constructs according to a variety of known methods (Agrobacterium Ti plasmids, electroporation, microinjection, microprojectile gun, etc). The transformed cells may then in suitable cases be regenerated into whole plants in which the new nuclear material is stably incorporated into the genome. Both transformed monocotyledonous and dicotyledonous plants may be obtained in this way, although the latter are usually more easy to regenerate. Some of the progeny of these primary transformants will inherit the recombinant DNA encoding the antifungal peptide(s).

The invention further provides a plant having improved resistance to a fungal pathogen and containing recombinant DNA which expresses an antifungal peptide according to the invention. Such a plant may be used as a parent in standard plant breeding crosses to develop hybrids and lines having improved fungal resistance.

Recombinant DNA is DNA, preferably heterologous, which has been introduced into the plant or its ancestors by transformation. The recombinant DNA encodes an antifungal peptide expressed for delivery to a site of pathogen attack (such as the leaves). The DNA may encode an active subunit of an antifungal peptide.

A pathogen may be any fungus growing on, in or near the plant. In this context, improved resistance is defined as enhanced tolerance to a fungal pathogen is when compared to a wild-type plant. Resistance may vary from a slight increase in tolerance to the effects of the pathogen (where the pathogen in partially inhibited) to total resistance so that the plant is unaffected by the presence of pathogen (where the pathogen is severely inhibited or killed). An increased level of resistance against a particular pathogen or resistance against a wider spectrum of pathogens may both constitute an improvement in resistance. Transgenic plants (or plants derived therefrom) showing improved resistance are selected following plant transformation or subsequent crossing.

Where the antifungal peptide is expressed within a transgenic plant or its progeny, the fungus is exposed to the peptide at the site of pathogen attack on the plant. In particular, by use of appropriate gene regulatory sequences, the peptide may be produced in vivo when and where it will be most effective. For example, the peptide may be produced within parts of the plant where it is not normally expressed in quantity but where disease resistance is important (such as in the leaves).

Examples of genetically modified plants which may be produced include field crops, cereals, fruit and vegetables such as: canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage, onion.

We have surprisingly found that when the peptides according to the invention are mixed with full length Rs-AFP2 a synergistic effect is observed where the antifungal activity of the mixture is better than that observed with the protein or the peptide on its own.

In a further aspect the invention provides an antifungal composition comprising a peptide according to the invention and Rs-AFP1 or Rs-AFP2.

The invention also extends to DNA constructs encoding both the antifungal peptide and Rs-AFP1 or Rs-AFP2, and to the use of said peptide mixtures in antifungal compositions for pharmaceutical, agricultural, and preservative applications.

The invention will now be described by way of example only, with reference to the following drawings wherein:

FIG. 9 shows the amino acid sequences of the proteins Hs-AFP1, Ah-AMP1 and Dm-AMP1.

FIG. 13 is an analysis of the results with overlapping 13–20-mer peptides within the region of 11e26-Phe49 from Rs-AFP2.

EXAMPLE 1

Production of Synthetic Peptides

Split peptides were synthesised by the PEPSCAN method. MPS peptides were synthesised by a Multiple Peptide Synthesis. All peptides were blocked at the amino terminal residue by an acetyl group and at the carboxy terminal residue by a carboxamide group.

PEPSCAN-split (C-termnal beta-alanine-amide). Radiation grafted polyethylene pins were functionalised with amino groups. Glycolic acid was coupled using dicyclohexylcarbodiimide (DCC) and after washing Boc-beta-alanine was coupled using DCC and dimethylaminopyridine (DMAP) as catalyst. In a block with pins, ten overlapping 15-mer peptides of AFP2 were synthesised simultaneously using Fmoc-amino acids and overnight couplings with DCC/Hydroxybenzotriazole (HOBt) as coupling method. The peptides were deprotected with a mixture of trifluoroacetic acid/phenol/thioanisole/water/ethanedithiol 10/0.75/0.5/0.5/0.25 (cleavage mixture B), then washed, dried, and finally cleaved from the pins using ammonia. This procedure yields peptides up to about lmg with C-terminal beta-alanine-amide.

PEPSCAN-split (C-terminal amide). Radiation grafted polyethylene pins were functionalised with hydroxyl groups. Boc-beta-alanine was coupled using DCC and DMAP as catalyst, the Boc group was removed with TFA and Fmoc-2,4-dimethoxy-4'(carboxymethyloxy)-benzhydrylamine (Rink linker) was coupled using the DCC/HOBt method. Next, 46 6-mer, 43 9-mer and 40 12-mer peptides from AFP2 were synthesised as described above in blocks containing 96 pins. After washing and drying the peptides were deprotected and cleaved with mixture B. The cleavage mixture was evaporated, extracted twice with diethylether, and lyophilised twice from water. This procedure yields peptides up to about lmg with a C-terminal amide.

Multiple Peptide Synthesis. We used a Hamilton Microlab 2200 to synthesise up to 40 peptides simultaneously at 15–30 umol scale. The Hamilton Microlab 2200 was programmed to deliver washing solvents and reagents to a rack with 20 or 40 individual 4 ml columns with filter containing resin for peptide synthesis. The columns were drained automatically after each step by vacuum. The coupling cycle was based on Fmoc/2-(1H-benzotriazol-1-yl)-1,1,3,3-tetramethyluronium hexafluorophosphate (HBTU) chemistry (Fields et al, Peptide Research 4, 1991 95–101) using double coupling steps. Peptides were deprotected and cleaved in two hours using 1.5 ml of mixture B and then precipitated twice by adding hexane/diethylether 1/1. The precipitate was dried and lyophilised from water/acetonitrile.

(a) Overlapping 15-mer Peptides Based on the Rs-AFP2 Protein

Figures 2, 11A:
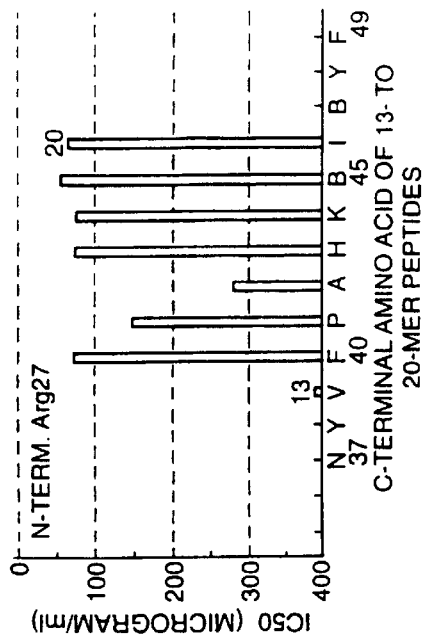
FIG. 2 shows the nucleotide sequence of the cDNA encoding Rs-AFP1.
FIG. 11a is a graphical representation showing the antifungal activity of Rs-AFP2-based 13–20-mers with same N-terminal residue Ile26-Ala31.
Figures 4, 11A:
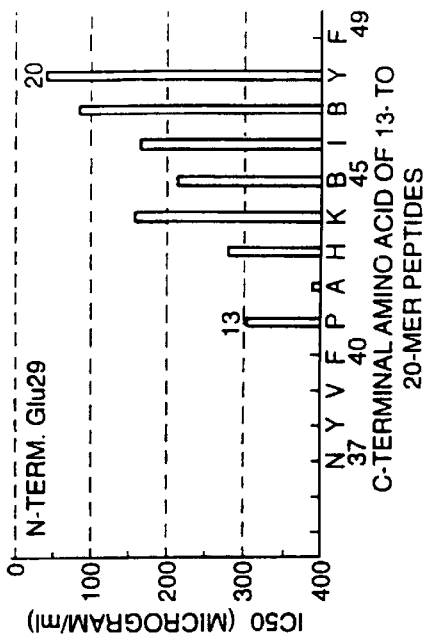

A set of ten split and MPS peptides were synthesised based on the primary sequence of the Rs-AFP2 protein. The sequences of the MPS peptides are shown in FIG. 3; the split peptides correspond to the MPS peptides with an additional C-terminal beta-alanine (an extra linker that was only used in the first PEPSCAN split synthesis). Each peptide consisted of fifteen amino acid residues identical to a run of amino acids in the Rs-AFP2 sequence:

PEPTIDE 1 had the sequence of Rs-AFP2 from amino acid position 1 to position 15;
PEPTIDE 2 had the sequence of Rs-AFP2 from amino acid position 5 to position 19;
PEPTIDE 3 had the sequence of Rs-AFP2 from amino acid position 9 to position 23;
PEPTIDE 4 had the sequence of Rs-AFP2 from amino acid position 13 to position 27;
PEPTIDE 5 had the sequence of Rs-AFP2 from amino acid position 17 to position 31;
PEPTIDE 6 had the sequence of Rs-AFP2 from amino acid position 21 to position 35;
PEPTIDE 7 had the sequence of Rs-AFP2 from amino acid position 25 to position 39;
PEPTIDE 8 had the sequence of Rs-AFP2 from amino acid position 29 to position 43;
PEPTIDE 9 had the sequence of Rs-AFP2 from amino acid position 33 to position 47;
PEPTIDE 10 had the sequence of Rs-AFP2 from amino acid position 37 to position 51.

(b) Overlapping 6-, 9- and 12-mer Peptides Based on the Rs-AFP2 Protein

Three sets of overlapping split peptides were synthesised by the PEPSCAN method based on the primary sequence of the Rs-AFP2 protein.

In the first set, each peptide consisted of six amino acid residues identical to a run of amino acids in the Rs-AFP2 sequence. The set of forty-six 6-mer peptides (numbered 1 to 46) covered the entire Rs-AFP2 sequence. For example, PEPTIDE 1 had the sequence of Rs-AFP2 from amino acid position 1 to position 6; PEPTIDE 2 had the sequence of Rs-AFP2 from amino acid position 2 to position 7: PEPTIDE 3 had the sequence of Rs-AFP2 from amino acid position 3 to position 8; PEPTIDE 45 had the sequence of Rs-AFP2 from amino acid position 45 to position 50; PEPTIDE 46 had the sequence of Rs-AFP2 from amino acid position 46 to position 51.

In the second set, each peptide consisted of nine amino acid residues identical to a run of amino acids in the Rs-AFP2 sequence. The set of forty-three 9-mer peptides (numbered 47 to 89) covered the entire Rs-AFP2 sequence. For example, PEPTIDE 47 had the sequence of Rs-AFP2 from amino acid position 1 to position 9; PEPTIDE 48 had the sequence of Rs-AFP2 from amino acid position 2 to position 10; PEPTIDE 49 had the sequence of Rs-AFP2 from amino acid position 3 to position 11; PEPTIDE 88 had the sequence of Rs-AFP2 from amino acid position 42 to position 50; PEPTIDE 89 had the sequence of Rs-AFP2 from amino acid position 43 to position 51.

In the third set, each peptide consisted of twelve amino acid residues identical to a run of amino acids in the Rs-AFP2 sequence. The set of forty 12-mer peptides (numbered 90 to 129) covered the entire Rs-AFP2 sequence. For example, PEPTIDE 90 had the sequence of Rs-AFP2 from amino acid position 1 to position 12; PEPTIDE 91 had the sequence of Rs-AFP2 from amino acid position 2 to position 13; PEPTIDE 92 had the sequence of Rs-AFP2 from amino acid position 3 to position 14; PEPTIDE 128 had the sequence of Rs-AFP2 from amino acid position 39 to position 50; PEPTIDE 129 had the sequence of Rs-AFP2 from amino acid position 40 to position 51.

Figure 4:
FIG. 4 is a diagram illustrating the sets of 6-, 9- and 12-mer Rs-AFP2 peptides.
Figure 5A:
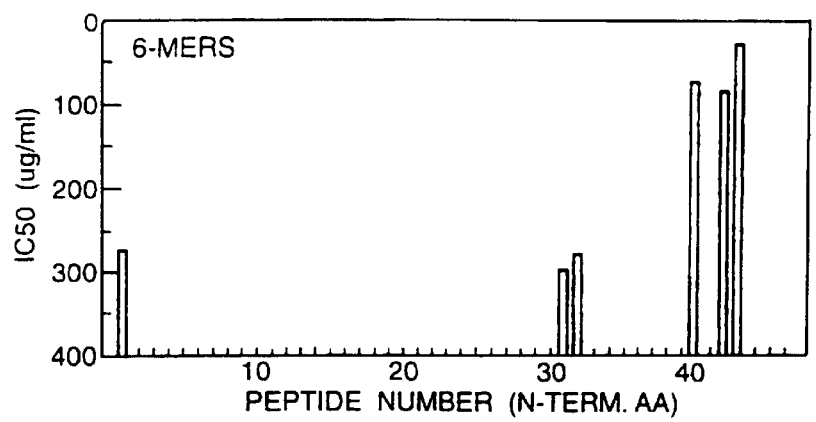
FIG. 5 is a graphical representation showing the antifungal activity of the Rs-AFP2-based 6-, 9- and 12-mer peptides.
Figure 5B:
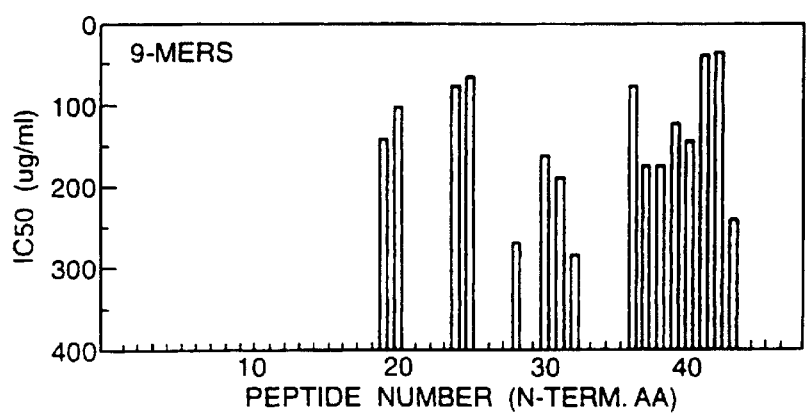
Figure 5C:
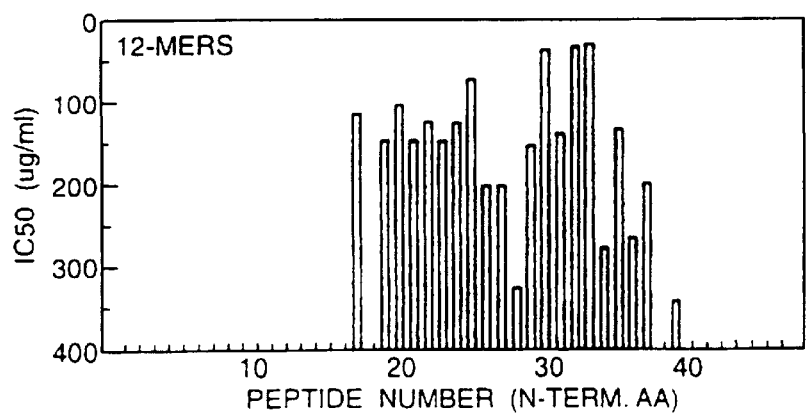
Figure 6A:
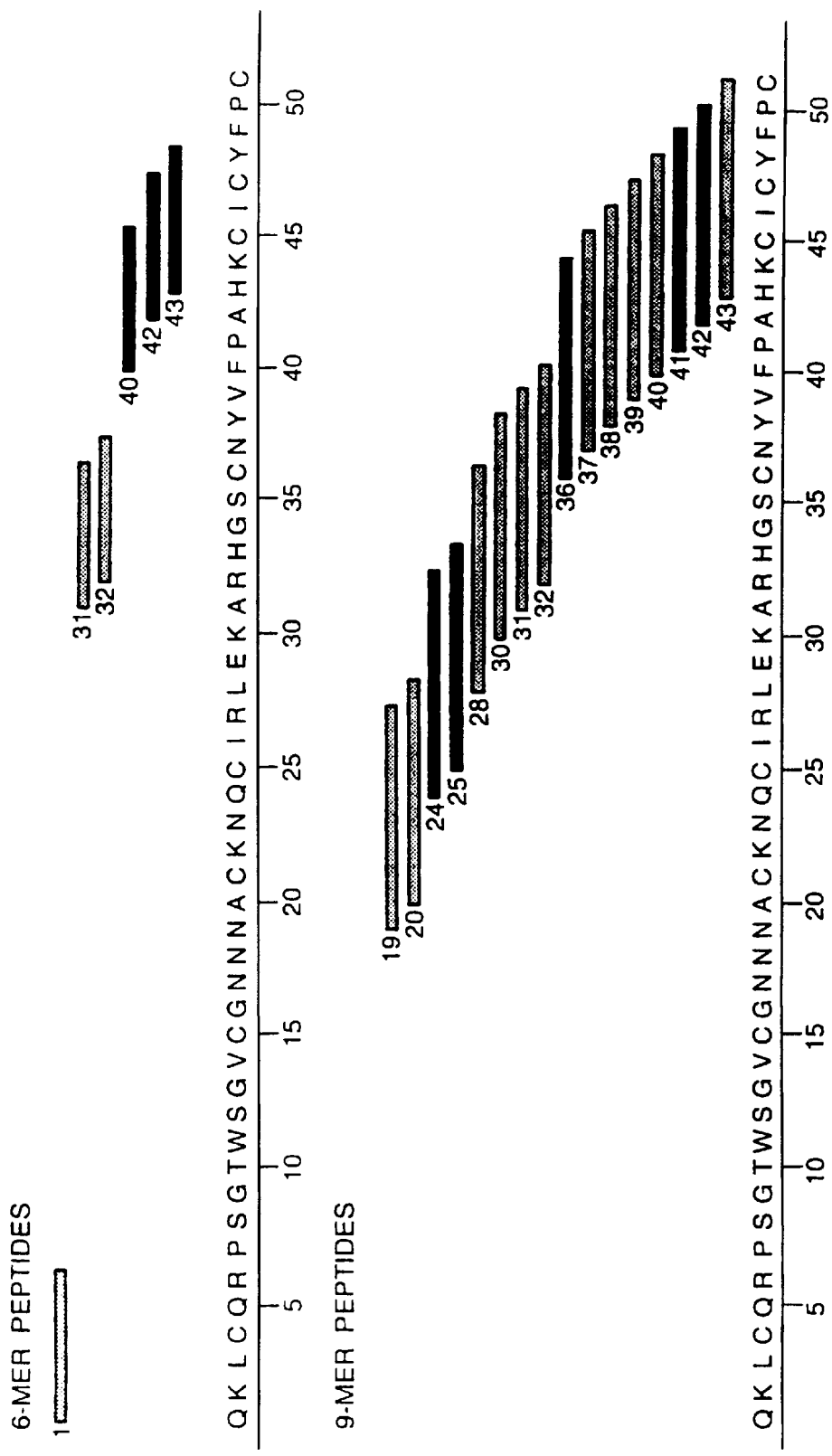
FIG. 6 is a diagram summarising all the active Rs-AFP2-based 6-mer, 9-mer, 12-mer and 15-mer peptides.
Figure 6B:
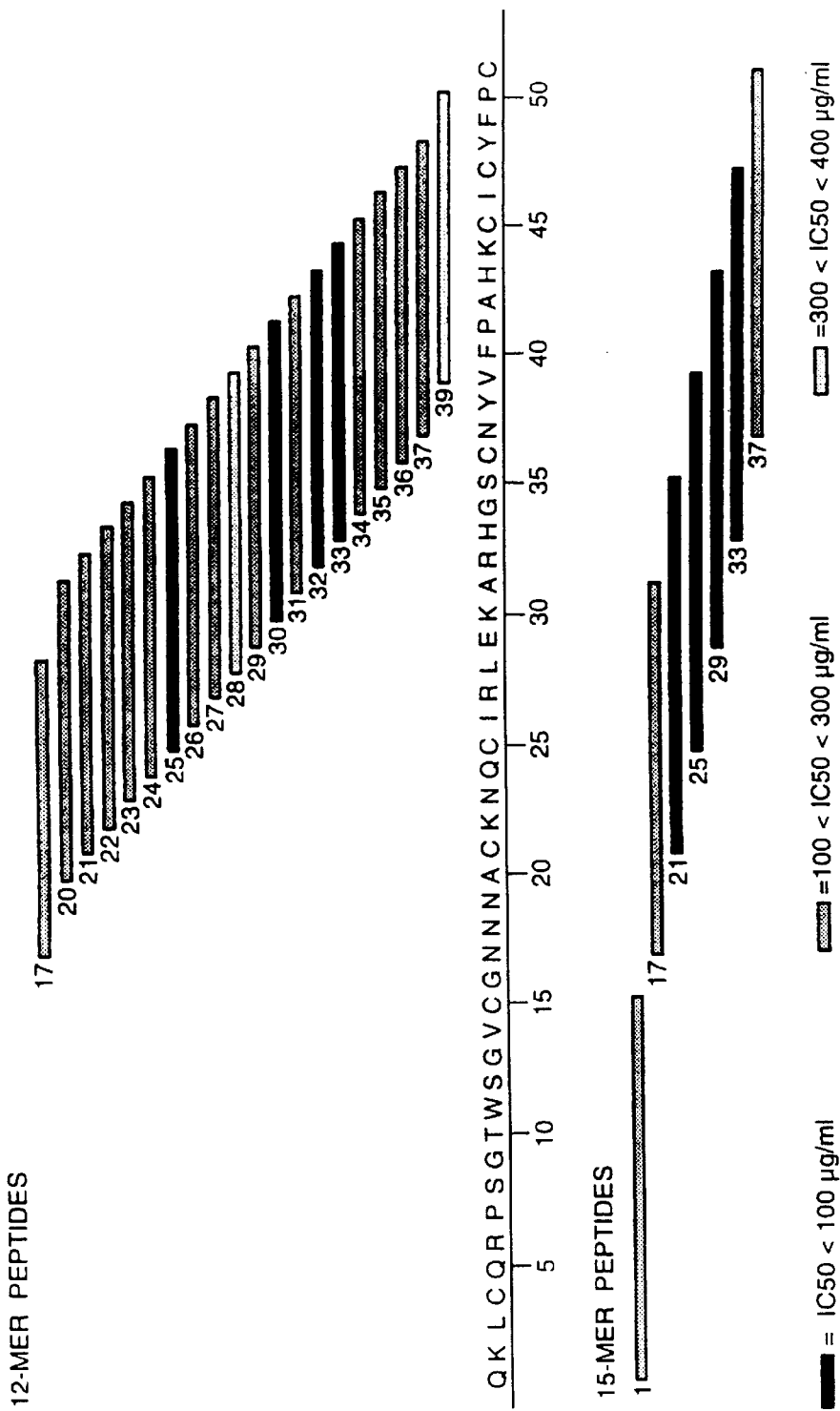

FIG. 4 is a visual representation of the sets of overlapping 6-, 9- and 12-mer peptides based on the sequence of Rs-AFP2.

(c) Overlapping 6-, 9- and 12-mer Peptides Based on the Rs-AFP1 Protein

Three sets of overlapping split peptides were synthesised by the PEPSCAN method based on the primary sequence of the Rs-AFP1 protein.

In the first set, each peptide consisted of six amino acid residues identical to a run of amino acids in the Rs-AFP1 sequence. The set of forty-six 6-mer peptides (numbered 1 to 46) covered the entire Rs-AFP1 sequence. For example, PEPTIDE 1 had the sequence of Rs-AFP1 from amino acid position 1 to position 6; PEPTIDE 2 had the sequence of Rs-AFP1 from amino acid position 2 to position 7; PEPTIDE 3 had the sequence of Rs-AFP1 from amino acid position 3 to position 8; PEPTIDE 45 had the sequence of Rs-AFP1 from amino acid position 45 to position 50; PEPTIDE 46 had the sequence of Rs-AFP 1 from amino acid position 46 to position 51.

In the second set, each peptide consisted of nine amino acid residues identical to a run of amino acids in the Rs-AFP1 sequence. The set of forty-three 9-mer peptides (numbered 47 to 89) covered the entire Rs-AFP1 sequence. For example, PEPTHDE 47 had the sequence of Rs-AFP1 from amino acid position 1 to position 9; PEPTIDE 48 had the sequence of Rs-AFP1 from amino acid position 2 to position 10; PEPTIDE 49 had the sequence of Rs-AFP1 from amino acid position 3 to position 11; PEPTIDE 88 had the sequence of Rs-AFP1 from amino acid position 42 to position 50; PEPTIDE 89 had the sequence of Rs-AFP1 from amino acid position 43 to position 51.

In the third set, each peptide consisted of twelve amino acid residues identical to a run of amino acids in the Rs-AFP1 sequence. The set of forty 12-mer peptides (numbered 90 to 129) covered the entire Rs-AFP1 sequence. For example, PEPTIDE 90 had the sequence of Rs-AFP1 from amino acid position 1 to position 12; PEPTIDE 91 had the sequence of Rs-AFP1 from amino acid position 2 to position 13; PEPTIDE 92 had the sequence of Rs-AFP1 from amino acid position 3 to position 14; PEPTIDE 128 had the sequence of Rs-AFP1 from amino acid position 39 to position 50; PEPTIDE 129 had the sequence of Rs-AFP1 from amino acid position 40 to position 51.

(d) Loop 1 Peptide Based on the Rs-AFP2 Protein

A further cyclic Rs-AFP2-based MPS peptide was synthesised. The loop 1 peptide consisted of ten amino acid residues identical to the Rs-AFP2 sequence between the cysteine residue at position 36 and the cysteine residue at position 45.

The loop 1 peptide has the following sequence: CNYVF-PAHKC. The peptide was cyclised via the two cysteines.

(e) 19-mer Peptides Based on the Rs-AFP2 Protein

Two further MPS peptides were synthesised.

Peptide G1 consisted of nineteen amino acid residues and had a sequence identical to the primary sequence of the Rs-AFP2 protein between positions 31 and 49. Peptide G1 has the sequence: ARHGSCNYVFPAHKCICYF.

Peptide G2 consisted of nineteen amino acid residues and had a sequence based on the primary sequence of the Rs-AFP2 protein between positions 31 and 49. To prevent dimerization or cyclization of the peptide, cysteine residues were replaced by alpha-aminobutyric acid (identified by the symbol B). Alpha-aminobutyric acid is a derivative with a side chain consisting of —CH2—CH3 which cannot form disulphide bonds. Peptide G2 has the sequence: ARHGS-BNYVFPAHKBIBYF.

f) Peptide J1, Based on the Ah-AMP1 Protein

A further MPS peptide was synthesised. Peptide J1 consisted of nineteen amino acid residues and had a sequence based on the primary sequence of Ah-AMP 1 shown in FIG. 9 between positions 30 and 48. To prevent dimerization or cyclization of the peptide, cysteine residues were replaced by alpha-aminobutyric acid (identified by the symbol B). Peptide J1 had the following sequence: ASHGABHKREN-HWKBFBYF.

(g) Peptide Handling and Storage

Peptides insoluble in water were dissolved in 50% acetonitrile: 50% acetonitrile was added to the peptide to give a stock solution which could be further diluted with water for fungal growth assays. Fungal growth was not affected by the presence of acetonitrile at the maximum concentration tested (20% v/v in the test well).

Split 15-mer peptides were dissolved in sterile milli-Q water to a final concentration of 5 mg/ml. MPS 15-mer peptides were dissolved to a final concentration between 4 and 10 mg/ml using acetonitrile as solvent for those peptides insoluble in water. Split 6-, 9- and 12-mer Rs-AFP1 peptides were dissolved to a final concentration of 2 mg/ml in 20% acetonitrile. Split 6-, 9- and 12-mer Rs-AFP2 peptides were dissolved to a final concentration of 2 mg/ml in sterile water except for peptides numbers 1 and 83 which were dissolved in 50% acetonitrile and numbers 3,4,5,25,47,52,64,69,70, 73,74,77,85 and 93 which were dissolved in 20% acetonitrile. Both Rs-AFP1 and Rs-AFP2 peptides were freeze-dried just before weighing. The loop 1 MPS peptide was completely soluble in water and dissolved at a concentration of 2 mg/ml.

De-aerated water and solvents were used to avoid peptide oxidation. Acetonitrile was deoxygenated with nitrogen; water was de-aerated by boiling for 20 minutes. Peptide solutions were stored at −20° C. under an atmosphere of nitrogen gas to avoid oxidation. Peptides that had been refrigerated were allowed to warm to room temperature before opening of the vials so as to avoid absorption of water.

EXAMPLE 2

Bioassays for Antifungal Activity: Methodology

The following fungal strains were used:

*Alternaria brassicicola* (MUCL 20297), *Ascophyta pisi* (MUCL 30164), *Botrytis cinerea* (MUCL 30158), *Fusarium culmorum* (IMI 180420) and *Verticillium dahliae* (MUCL 19210). Fungi were grown on six cereal agar plates at room temperature and under white fluorescent light except for *F culmorum* and *V dahliae* which were grown in the dark. The duration of the spore harvest varied between 10 and 25 days depending on the strain. Spores were collected as follows. Five to ten ml of sterile milli-Q water was poured into each dish and the surface of the agar was rubbed with a sterile spatula to obtain a suspension containing mycelium and spores. This suspension was filtered through a sterile glasswool-plugged funnel and the filtrate containing the spores was collected in a sterile polypropylene centrifuge tube. The *A brassicicola* spores were suspended in sterile 0.1% Tween 20 (Merk, 822184) due to their hydrophobic nature. The spore suspensions were then washed twice by centrifugation at 2,400×g for 15 minutes and resuspended in a small volume of steril milli-Q water. The spore density was determined in a counting chamber and then adjusted to $4\times10^7$ spores per ml. Aliquots of the spore suspension were transferred to sterile microtubes and an equal volume of sterile 50% glycerol (Merck, 4091) was added to each tube so that a final spore suspension of $2\times10^7$ spores per ml in 25% glycerol was obtained. After careful mixing of the stock, the spore suspension was transferred in 100 µl aliquots to sterile microtubes and stored at −80° C.

Antifungal activity was measured by photospectrometry as described by Broekaert et al, (1990, FEMS Microbiol Lett, 69:55–60). Tests were performed by adding 20 µl of test solution and 80 µl of a fungal spore suspension ($2\times10^4$ spores/ml) per well in a sterile flat-bottom 96-well microtiterplate. The spore suspension was prepared by diluting the stock spore suspension ($10^7$ spores/ml in 25% glycerol) 1:1000 in half-strength potato dextrose broth. A positive growth control consisting of eight wells containing 20 µl of sterile milli-Q water and 80 µl of the fungal spore suspension was included in each test. The microtiterplates were incubated (with the lid on) in an aerated place at room temperature and under conditions of darkness for all test organisms.

After 30 minutes of incubation (when the spores are settled on the well bottom) the optical density was measured in a microplate reader (Bio Rad 3550-UV) at 595 nm. Incubation of the microtiterplates continued until the optical density of the control microculture was between 0.250 and 0.500, which took approximately 72 hours (96 hours for *V dahliae*). Percentage of growth inhibition (% GI) was estimated as 100 times the ratio of the corrected absorbance of the control microculture minus the corrected absorbance of the test microculture over the corrected absorbance of the control microculture at 595 nm. The corrected absorbance values equal the absorbance at 595 nm of the culture measured after 72 or 96 hours minus the absorbance at 595 nm measured after 30 minutes.

$$\%GI=[(A_{control}-A_{test})/A_{control}]\times 100$$

where $A_{control}=(A_{72/96h}-A_{30min})_{control}$ $A{test}=(A_{72/96h}-A_{30min})_{test}.$ The IC50 value is defined as the concentration that gives a 50% growth inhibition after 72 or 96 hours of incubation. The minimum inhibitory concentration (MIC) corresponds to the minimum concentration that gives 100% growth inhibition after 72 or 96 hours incubation.

The composition of the different culture media used in the bioassays is given below:

Six Cereal Agar (6CA)

20 g Bambix (Nutricia), 15 g Agar Technical (Oxoid L13), 1l milli-Q water, sterilized for 15 minutes at 121° C.

SMF 285 mg (2.5 mM K$^+$) K$_2$HPO$_4$.3H$_2$O, 12.5 mg (50 µM Mg$^{2+}$) MgSO$_4$.7H$_2$O, 7.3 mg (50 µM Ca$^{2+}$) CaCl$_2$.2H$_2$O, 1.14 mg (5 µM Fe$^{2+}$) FeSO$_4$.7H$_2$O, 0.023 mg (0.1 µM Co$^{2+}$) CoCl$_2$.6H$_2$O, 0.024 mg (0.1 µM Cu$^{2+}$) CuSO$_4$.5H$_2$O, 0.24 mg (2 µM Na+) Na$_2$MoO$_4$.2H$_2$O, 0.03 mg (0.5 µM BO$^{3+}$) H$_3$BO$_3$, 0.01 mg (0.1 µM K$^+$) KI, 0.14 mg (0.5 µM Zn$^+$) ZnSO$_4$.7H$_2$O, 0.01 mg (0.1 µM Mn$^{2+}$) MnSO$_4$.1H$_2$O, 10 g glucose, 1 g asparagine, 20 mg methionine, 20 mg myo-inositol, 2 mg biotine, 10 mg thiamine-HCl, 2 mg piridoxine, 1l milli-Q water; sterilized by filtration on 0.22 µm filters and stored at 4° C.

SMF+

SMF medium supplemented with 1 mM Ca$^{2+}$ and 50 mM K$^+$.

Half Strength Potato Dextrose Broth (½ PDB)

12 g PDB (Difco 0549-01-7), 1l milli-Q water; sterilized for 15 minutes at 121° C.

1/16 Potato Dextrose Broth (1/16 PDB)

1.5 g PDB (Difco 0549-01-7), 1l milli-Q water; sterilized for 15 minutes at 121° C.

EXAMPLE 3

Antifungal Activity of the 15-mer Peptides

The split peptides were tested for their antifungal activity on *F culmorum*. Each peptide was tested in a twofold dilution series starting from 500 µg/ml down to 3.9 µg/ml and each test was carried out in duplicate. The results given in Table 1 are a combination of microscopic analysis and optical density determination. Only peptides 6, 7, 8 and 9 showed a clear antifungal activity with minimum inhibitory concentration (MIC) values of around 30 μg/ml (peptide 6), 60 μg/ml (peptide 7) and 15 μg/ml (peptides 8 and 9). Due to the partial solubility of the peptides, the initial test concentrations are only approximations and hence the MIC values are approximations.

The MPS peptides were tested on five different fungal strains: *A brassiciciola, A pisi, B cinerea, F culmorum* and *V dahliae*. Each peptide was tested in a twofold dilution series starting from 500 μg/ml down to 3.9 μg/ml. The test was carried out five times with *F culmorum* and once with the other fungi. The same stock dry peptide was used for all tests but the peptide solutions were different, one solution being used for a maximum of three tests. The results shown in Table 1 correspond to the medium value for the various tests: the variability of results between tests was of an order of two. The sensitivity of the different fungi to the presence of peptides varied, *V dahliae* being the most sensitive and *B cinerea* being the least sensitive. However, peptides 6, 7, 8 and 9 were the most potent antifungal peptides on all the test organisms with MIC values varying from 31.25 to 250 μg/ml depending on the fungus.

Figures 1, 11A:
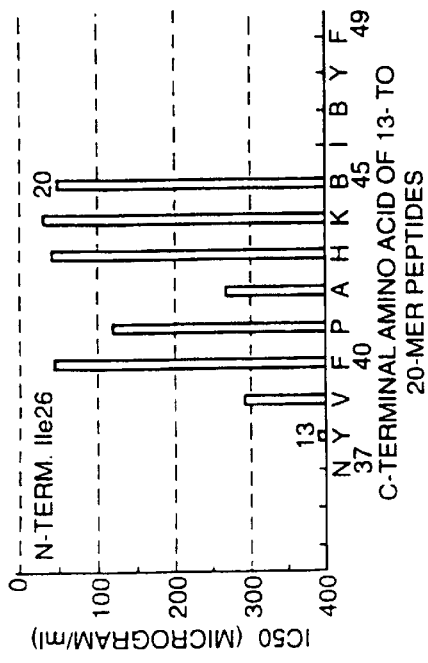
FIG. 1 shows the amino acid sequences of some plant defensins.
Figures 3, 11A:
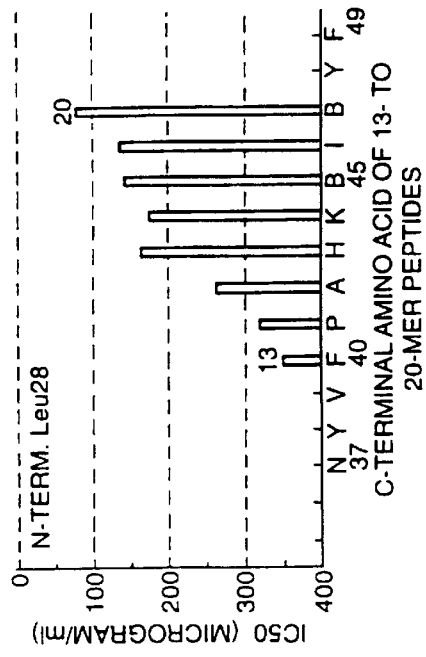
FIG. 3 shows the amino acid sequences of the 15-mer Rs-AFP2 peptides.

Peptides 6, 7, 8 and 9 each comprise fifteen amino acid residues identical to a run of fifteen amino acid residues found between position 21 and position 47 of the Rs-AFP2 sequence shown in FIG. 1. These tests show that peptides 6, 7, 8 and 9 have antifungal activity.

TABLE 1

| | MIC VALUES (μg/ml) | | | | | |
|---|---|---|---|---|---|---|
| | F CULMORUM | | A BARASSICIC- | | | |
| PEPTIDE | Split | MPS | OLA | A PISI | B CINEREA | V DAHLIAE |
| 1 | 250 | 250–500 | 250 | >500 | >500 | 250 |
| 2 | >500 | >500 | >500 | >500 | >500 | >500 |
| 3 | >500 | 250 | >500 | >500 | 500 | 500 |
| 4 | >500 | 125 | 500 | >500 | 250 | 125 |
| 5 | 250–500 | 125–250 | 125 | 500 | 500 | 250 |
| 6 | 31.25 | 62.5 | 62.5 | 125 | 250 | 31.25 |
| 7 | 31.25–62.5 | 62.5 | 62.5 | 250 | 250 | 31.25 |
| 8 | 15.625 | 31.25–62.5 | 31.25 | 125 | 250 | 31.25 |
| 9 | 15.625 | 31.25–62.5 | 62.5 | 250 | 250 | 31.25 |
| 10 | 125–250 | 500 | >500 | >500 | >500 | 250 |
| Rs-AFP2 | 10 | 5–10 | 10 | 20–40 | >40 | 10 |

EXAMPLE 4

Antifungal Activity of the 6-, 9- and 12-mer Rs-AFP2 Peptides

The 6-, 9- and 12-mer Rs-AFP2 split peptides were tested for their antifungal activity on *F culmorum*. Each peptide was tested in a twofold dilution series starting form 400 μg/ml down to 3.1 μg/ml using the medium ½ PDB. Rs-AFP2 was used in all the plates as a positive control, in a twofold dilution series starting from 40 μg/ml down to 0.31 μg/ml. The tests were carried out in duplicate for the 6-mer peptides (numbered 1 to 46) and for the 9-mer peptides (numbered 47 to 89) and in triplicate for the 12-mer peptides (numbered 90 to 129). Tables 2, 3 and 4 show the results for the active peptides only.

TABLE 2

| 6-MER PEPTIDES | | |
|---|---|---|
| PEPTIDE | MIC (μg/ml) | IC50 (μg/ml) |
| 1 | 400 | 268 |
| 31 | 400 | 297 |
| 32 | 400 | 279 |
| 40 | 100 | 72 |
| 42 | 100 | 83 |
| 43 | 50 | 28 |

TABLE 3

| 9-MER PEPTIDES | | |
|---|---|---|
| PEPTIDE | MIC (μg/ml) | IC50 (μg/ml) |
| 65 | 200 | 144 |
| 66 | 150 | 105 |
| 70 | 100 | 78 |
| 71 | 100 | 66 |
| 74 | 400 | 270 |
| 76 | 300 | 162 |
| 77 | 300 | 189 |
| 78 | 400 | 284 |
| 82 | 100 | 77 |
| 83 | 250 | 175 |
| 84 | 400 | 175 |
| 85 | 200 | 121 |

TABLE 3-continued

| 9-MER PEPTIDES | | |
|---|---|---|
| PEPTIDE | MIC (μg/ml) | IC50 (μg/ml) |
| 86 | 400 | 144 |
| 87 | 50 | 39 |
| 88 | 50 | 35 |
| 89 | 400 | 242 |

TABLE 4

12-MER PEPTIDES

| PEPTIDE | MIC (μg/ml) | IC50 (μg/ml) |
|---|---|---|
| 106 | 150 | 116 |
| 108 | 200 | 150 |
| 109 | 150 | 106 |
| 110 | 200 | 148 |
| 111 | 200 | 126 |
| 112 | 200 | 149 |
| 113 | 200 | 127 |
| 114 | 100 | 74 |
| 115 | 300 | 203 |
| 116 | 400 | 202 |
| 117 | >400 | 327 |
| 118 | 200 | 154 |
| 119 | 50 | 37 |
| 120 | 200 | 139 |
| 121 | 50 | 33 |
| 122 | 50 | 30 |
| 123 | 300 | 280 |
| 124 | 200 | 135 |
| 125 | 400 | 265 |
| 126 | 300 | 201 |
| 128 | >400 | 344 |

Figures 6, 11A:
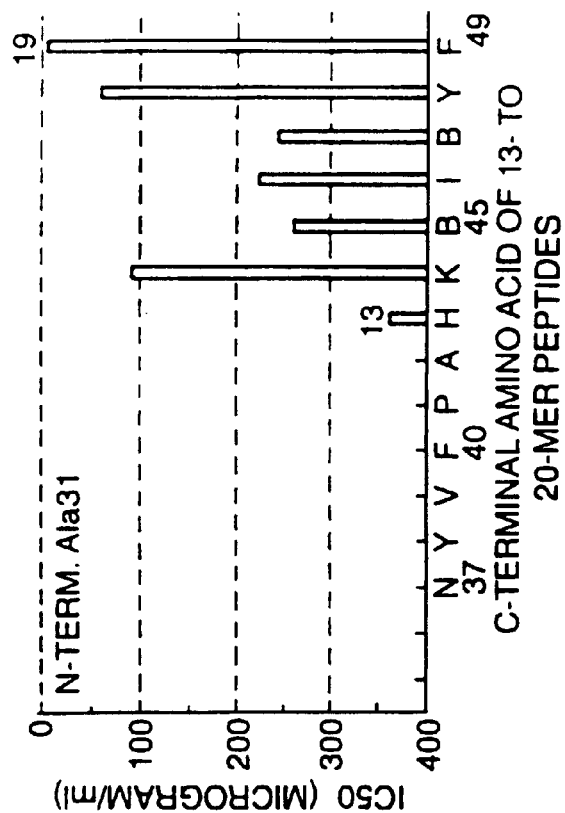
Figures 5, 11A:
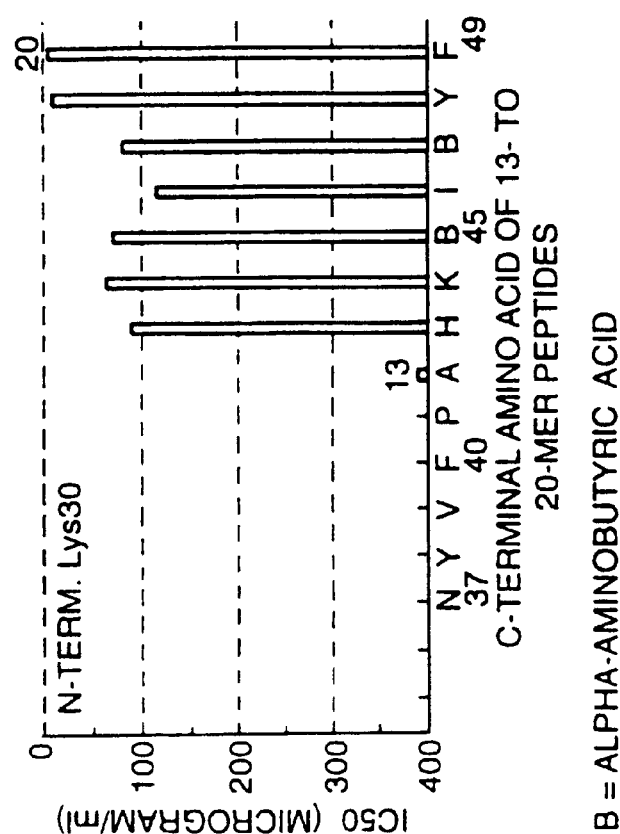
Figures 5, 6, 11B:
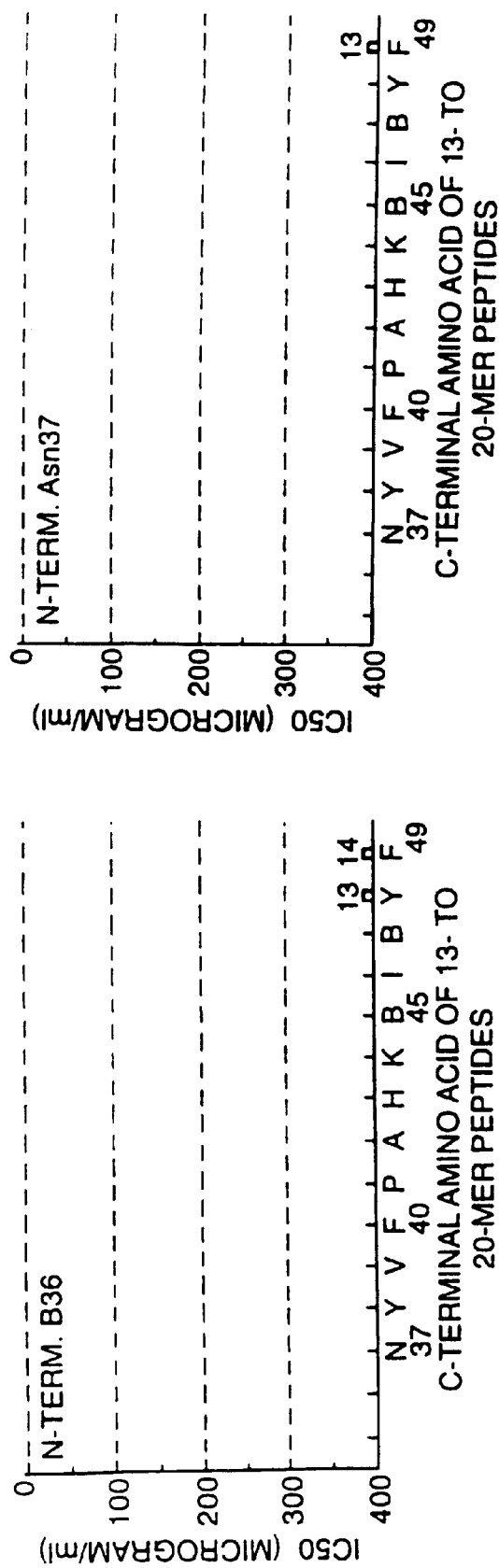
FIG. 11b is a graphical representation showing the antifungal activity of Rs-AFP2-based 13–20-mers with same N-terminal residue Arg32-Asn37.
Figures 1, 12A:
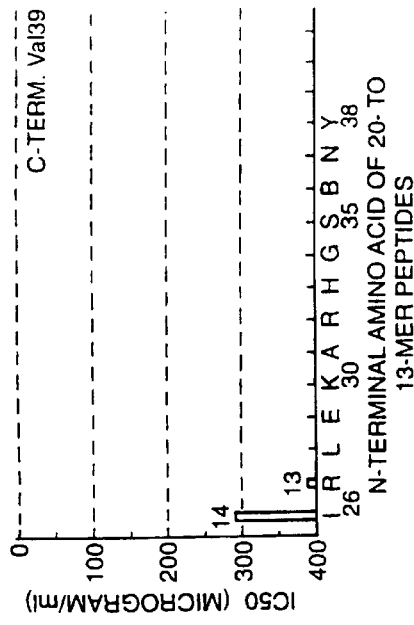
FIG. 12a is a graphical representation showing the antifungal activity of Rs-AFP2-based 13–20-mers with same C-terminal residue Tyr38-His43.
Figures 2, 12A:
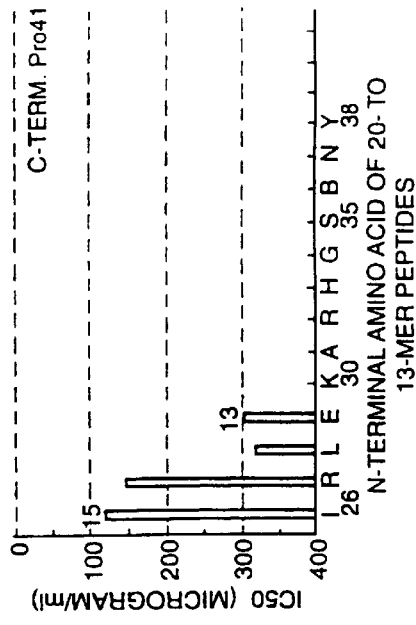
Figures 3, 12A:
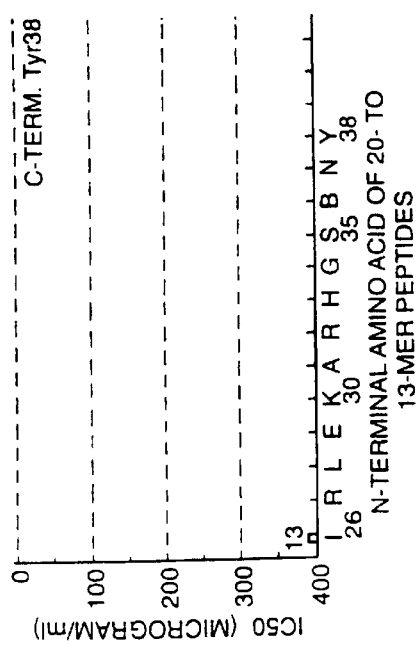
Figures 4, 12A:
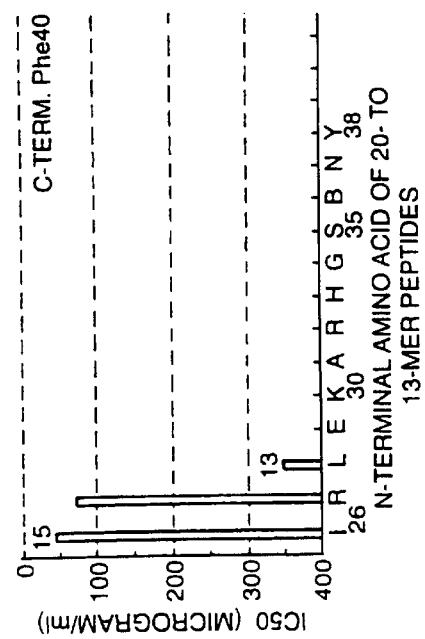
Figures 5, 6, 12A:
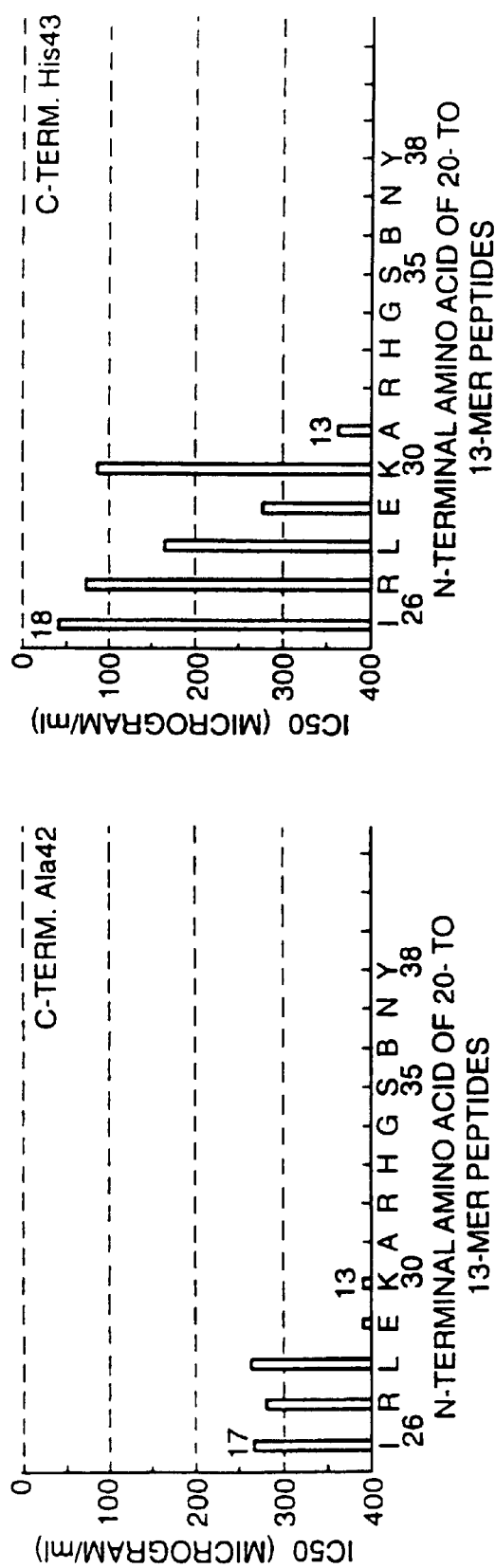
Figures 1, 2, 3, 4, 12B:
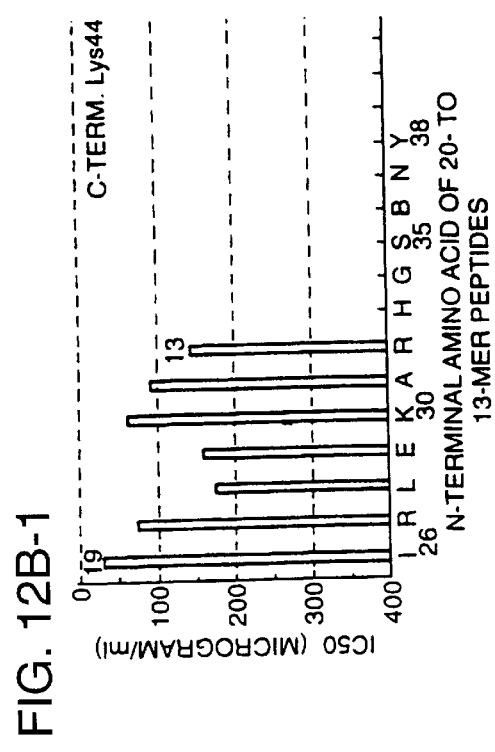
FIG. 12b is a graphical representation showing the antifungal activity of Rs-AFP2-based 13–20-mers with same C-terminal residue Lys44-Phe49.
Figures 6, 12B:
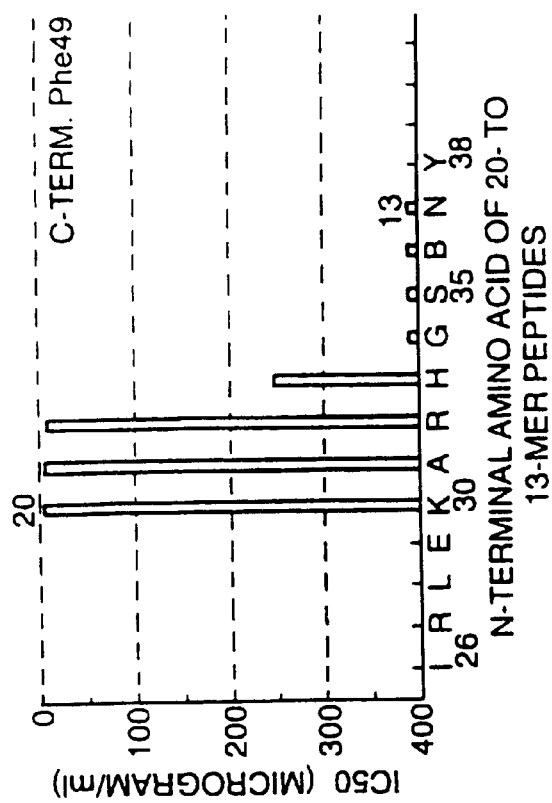
Figures 5, 12B:
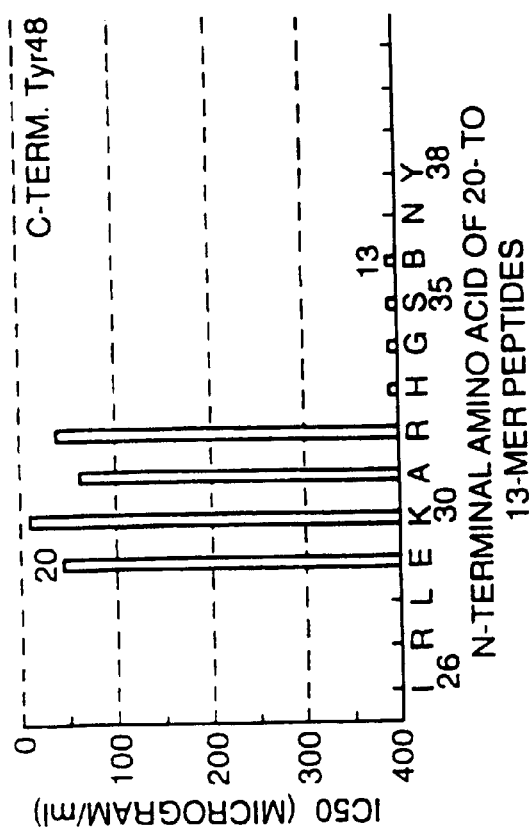

FIG. 5 is a graphical representation of the results showing the antifungal activity of the Rs-AFP2-based 6-, 9- and 12-mer peptides. Active peptides are indicated by bars in the graphs of IC50 value (μg/ml) against peptide number which are given for each set of peptides. In the graph for the 9-mer peptide set, peptides are numbered according to their N-terminal amino acid so that, for example, peptide number 1 in the FIG. 5 9-mer graph corresponds to peptide 47 and peptide number 43 in the FIG. 5 9-mer graph corresponds to peptide number 89 in Table 3. Similarly, in the graph for the 12-mer peptide set, peptides are numbered according to their N-terminal amino acid so that, for example, peptide number 1 in the FIG. 5 12-mer graph corresponds to peptide 90 and peptide number 39 in the FIG. 5 12-mer graph corresponds to peptide number 128 in Table 4.

FIG. 6 is a diagram summarising all the active 6-mer, 9-mer and 12-mer peptides. Peptides are once again numbered according to their N-terminal amino acid. Each of the active peptides has been categorised according to its IC50 value, as follows.

In the 6-mer peptide set, peptide numbers 1, 31 and 32 have an IC50 value between 100 and 300 μg/ml while peptide numbers 40, 42 and 43 have an IC50 value less than 100 μg/ml.

In the 9-mer peptide set, peptide numbers 19, 20, 28, 30 to 32, 37 to 40 and 43 have an IC50 value between 100 and 300 μg/ml while peptide numbers 24, 25, 36, 41 and 42 have an IC50 value less than 100 μg/ml (equivalent to peptides 70, 71, 82, 87 and 88 in Table 3).

In the 12-mer peptide set, peptide numbers 28 and 39 have an IC50 value between 300 and 400 μg/ml, peptide numbers 17, 20 to 24, 26, 27, 29, 31 and 34 to 37 have an IC50 value between 100 and 300 μg/ml while peptides 25, 30, 32 and 33 have an IC50 value less than 100 μg/ml (equivalent to peptides 114, 119, 121 and 122 in Table 4).

FIG. 6 also shows the active 15-mer peptides. Peptide 1 (N-terminal amino acid corresponding to position 1 in the Rs-AFP2 sequence), peptide 5 (N-terminal amino acid corresponding to position 17 in the Rs-AFP2 sequence) and peptide 10 (N-terminal amino acid corresponding to position 37 in the Rs-AFP2 sequence) have an IC50 value between 100 and 300 μg/ml. Peptide 6 (N-terminal amino acid corresponding to position 21 in the Rs-AFP2 sequence), peptide 7 (N-terminal amino acid corresponding to position 25 in the Rs-AFP2 sequence), peptide 8 (N-terminal amino acid corresponding to position 29 in the Rs-AFP2 sequence) and peptide 9 (N-terminal amino acid corresponding to position 33 in the Rs-AFP2 sequence) have an IC50 value less than 100 μg/ml.

The antifungal activity of the peptides is reduced by the presence of inorganic salts (1 mM $CaCl_2$ or 50 mM KCl) in the growth medium. The antagonistic effect of cations has previously been reported for Rs-AFPs (Terras et al, 1992, J Biol Chem. 267:1–9) although the cation sensitivity seems to vary largely with the test fungus used.

EXAMPLE 5

Antifungal Activity of the 6-, 9- and 12-mer Rs-AFP1 Peptides

The 6-, 9- and 12-mer Rs-AFP1 split peptides were tested for their antifungal activity on *F culmorum* and on *Ascophyta pisi*. Each peptide was tested in a twofold dilution series starting form 400 μg/ml down to 3.1 μg/ml using the medium ½PDB. Rs-AFP2 was used in all the plates as a positive control, in a twofold dilution series starting from 40 μg/ml down to 0.31 μg/ml. The tests were carried out in duplicate for *F culmorum* and once for *A pisi*. The MIC and IC50 values are the average values of two or three experiments, the results being a combination of microscopic analysis and optical density determination. Tables 5, 6 and 7 show the results for the active peptides only. The 6-mer peptides are numbered 1 to 46, the 9-mer peptides are numbered 47 to 89 and the 12-mer peptides are numbered 90 to 129.

TABLE 5

6-MER PEPTIDES

| PEPTIDE | F CULMORUM | | A PISI | |
|---|---|---|---|---|
| | MIC (μg/ml) | IC50 (μg/ml) | MIC (μg/ml) | IC50 (μg/ml) |
| 31 | 400 | 266 | — | — |
| 42 | 100 | 61 | 400 | 267 |
| 43 | 75 | 38 | >400 | 340 |
| 44 | >400 | 376 | >400 | 400 |

TABLE 6

9-MER PEPTIDES

| PEPTIDE | F CULMORUM | | A PISI | |
|---|---|---|---|---|
| | MIC (μg/ml) | IC50 (μg/ml) | MIC (μg/ml) | IC50 (μg/ml) |
| 74 | >400 | 370 | — | — |
| 76 | 250 | 169 | >400 | 342 |
| 77 | 300 | 193 | 200 | 143 |
| 78 | 100 | 69 | 100 | 70 |
| 82 | 150 | 113 | 400 | 265 |
| 83 | 400 | 330 | — | — |
| 84 | 250 | 145 | — | — |
| 85 | 200 | 121 | 400 | 184 |
| 86 | 250 | 196 | 200 | 80 |
| 87 | 37.5 | 28 | 50 | 31 |
| 88 | 37.5 | 21 | 25 | 18 |
| 89 | 400 | 233 | 100 | 70 |

TABLE 7

12-MER PEPTIDES

| PEPTIDE | F CULMORUM | | A PISI | |
|---|---|---|---|---|
| | MIC (µg/ml) | IC50 (µg/ml) | MIC (µg/ml) | IC50 (µg/ml) |
| 110 | 400 | 223 | — | — |
| 113 | 400 | 362 | — | — |
| 114 | 400 | 328 | >400 | 318 |
| 116 | 400 | 359 | — | — |
| 117 | 400 | 347 | 400 | 293 |
| 118 | 100 | 63 | 200 | 91 |
| 119 | 50 | 33 | 100 | 66 |
| 120 | 150 | 105 | 200 | 126 |
| 121 | 50 | 38 | 100 | 55 |
| 122 | 50 | 35 | 100 | 74 |
| 123 | 300 | 266 | >400 | 349 |
| 124 | 300 | 213 | >400 | 318 |
| 125 | >400 | 350 | 400 | 281 |
| 126 | 300 | 189 | 400 | 298 |
| 127 | >400 | 354 | 400 | 302 |
| 128 | >400 | 320 | 400 | 181 |
| 129 | — | — | 400 | 311 |

Figure 7A:
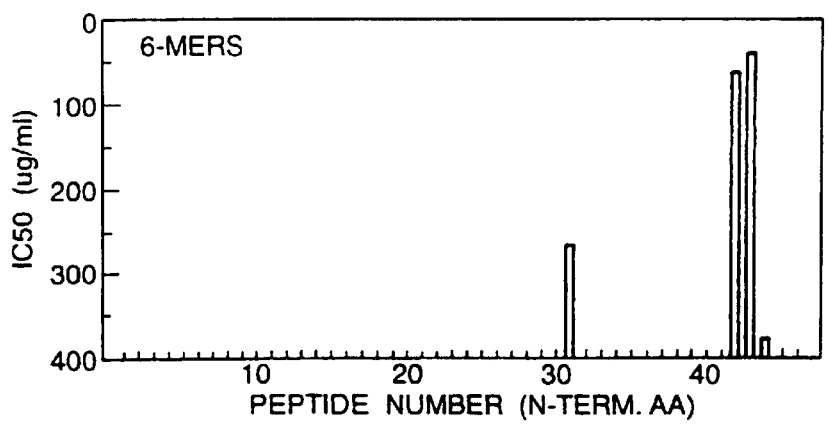
FIG. 7 is a graphical representation showing the antifungal activity of the Rs-AFP 1-based 6-, 9- and 12-mer peptides.
Figure 7B:
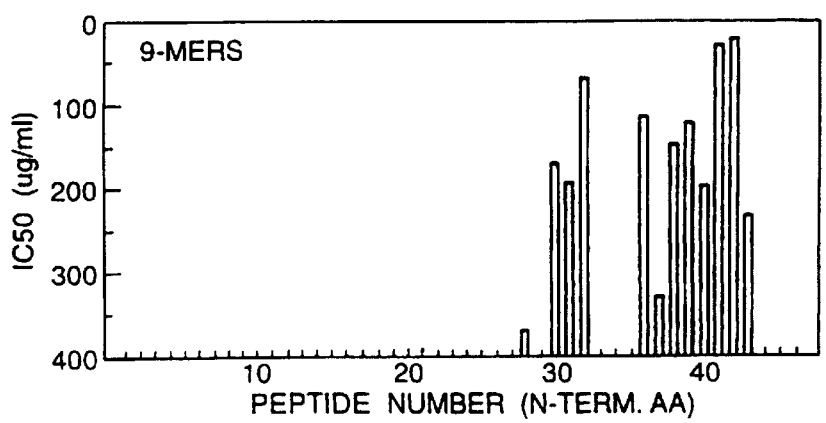
Figure 7C:
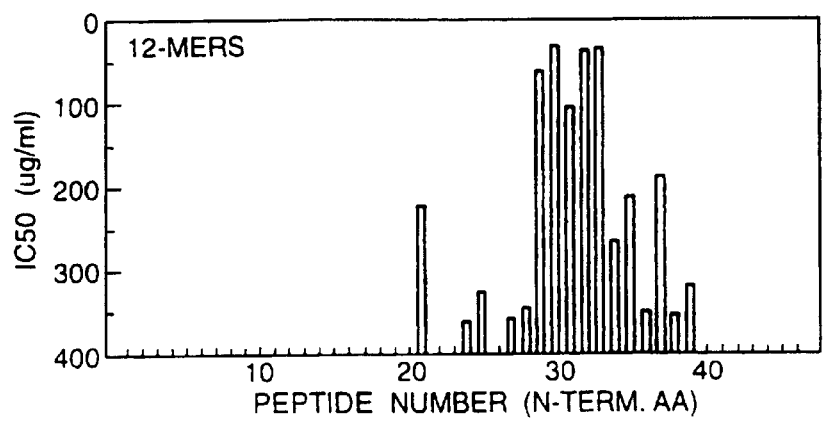

FIG. 7 is a graphical representation of the results showing the antifungal activity of the Rs-AFP1-based 6-, 9- and 12-mer peptides on F culmorum. Active peptides are indicated by bars in the graphs of IC50 value (µg/ml) against peptide number which are given for each set of peptides. In the graph for the 9-mer peptide set, peptides are numbered according to their N-terminal amino acid so that, for example, peptide number 1 in the FIG. 7 9-mer graph corresponds to peptide 47 and peptide number 43 in the FIG. 7 9-mer graph corresponds to peptide number 89 in Table 6. Similarly, in the graph for the 12-mer peptide set, peptides are numbered according to their N-terminal amino acid so that, for example, peptide number I in the FIG. 7 12-mer graph corresponds to peptide 90 and peptide number 39 in the FIG. 7 12-mer graph corresponds to peptide 128 in Table 7.

Figure 8A:
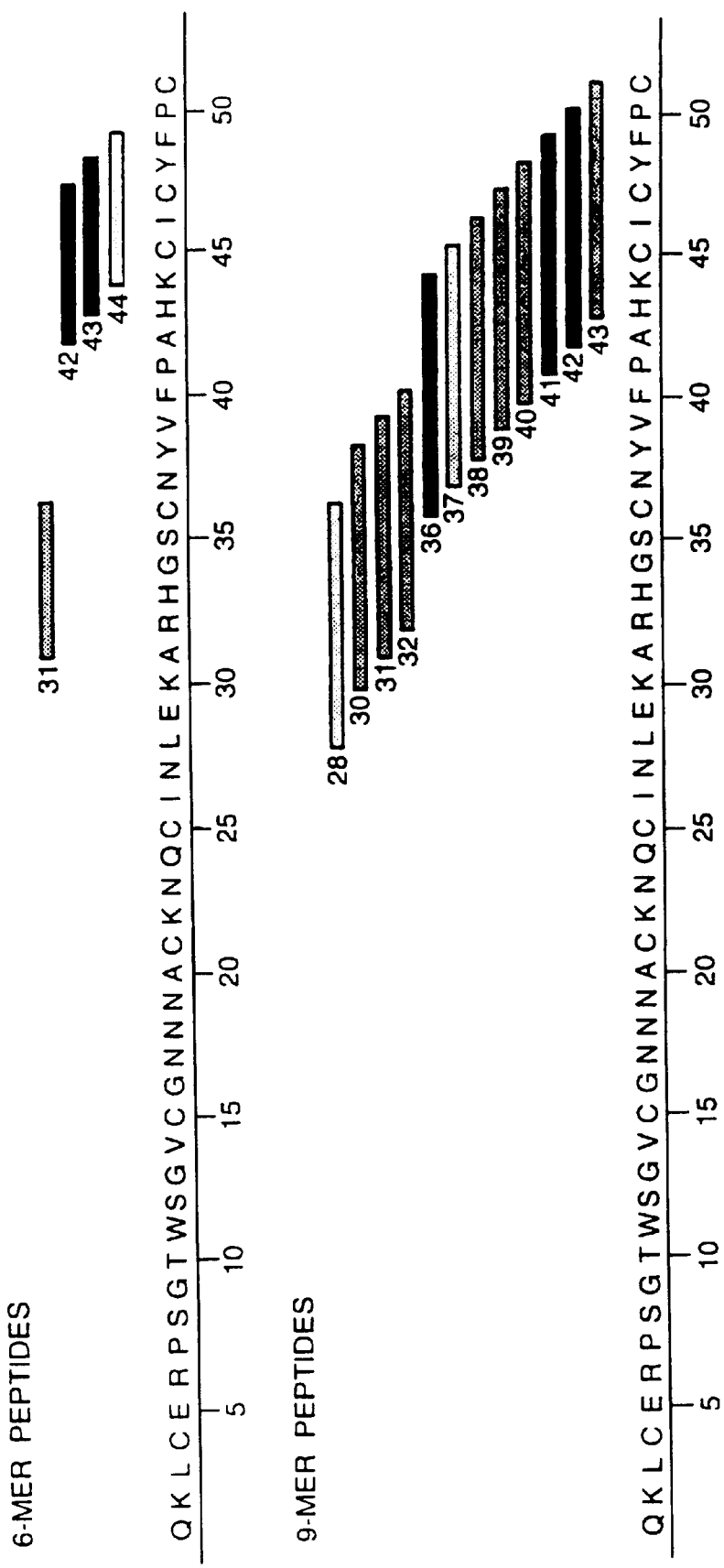
FIG. 8 is a diagram summarising all the active Rs-AFP 1-based 6-mer, 9-mer and 12-mer peptides.
Figure 8B:
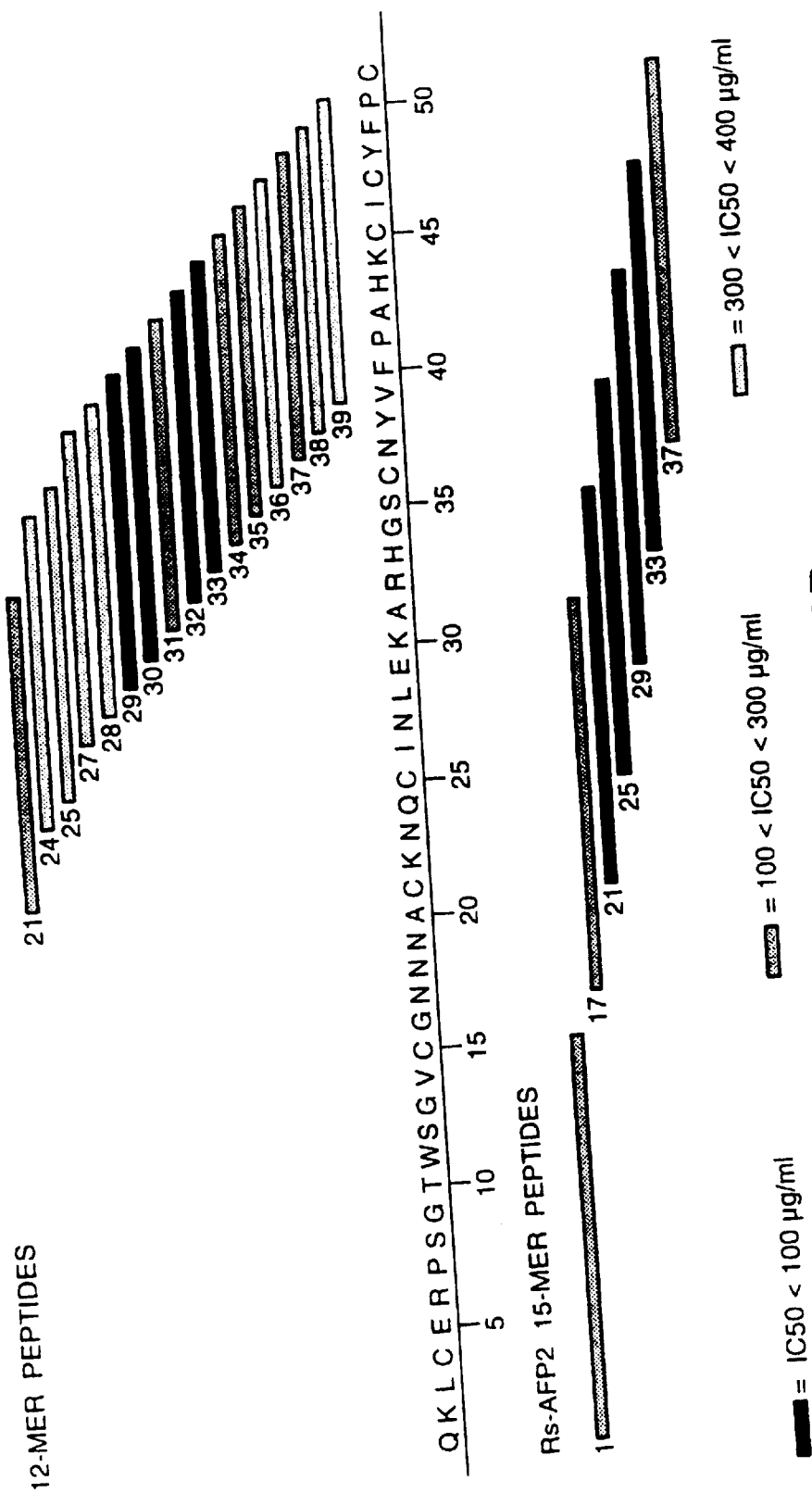

FIG. 8 is a diagram summarising the 6-mer, 9-mer and 12-mer peptides which are active on F culmorum. Peptides are once again numbered according to their N-terminal amino acid. Each of the active peptides has been categorised according to its IC50 value, as follows.

In the 6-mer peptide set, peptide number 44 has an IC50 value between 300 and 400 µg/ml, peptide number 31 has an IC50 value between 100 and 300 µg/ml while peptide numbers 42 and 43 have an IC50 value less than 100 µg/ml.

In the 9-mer peptide set, peptide numbers 28 and 37 have an IC50 value between 300 and 400 µg/ml, peptide numbers 30, 31, 36, 38 to 40 and 43 have an IC50 value between 100 and 300 µg/ml while peptide numbers 32, 41 and 42 have an IC50 value less than 100 µg/ml (equivalent to peptides 78, 87 and 88 in Table 6). On A pisi two further 9-mer peptides have an IC50 value less than 100 µg/ml: peptide number 40 (equivalent to peptide 86 in Table 6) and peptide number 43 (equivalent to peptide 89 in Table 6).

In the 12-mer peptide set, peptide numbers 24 to 28, 36, 38 and 39 have an IC50 value between 300 and 400 µg/ml, peptide numbers 21, 31, 34, 35 and 37 have an IC50 value between 100 and 300 µg/ml while peptides 29, 30, 32 and 33 have an IC50 value less than 100 µg/ml (equivalent to peptides 118, 119, 121 and 122 in Table 7).

FIG. 8 also shows the active Rs-AFP2-based 15-mer peptides as a comparison. Peptide 1 (N-terminal amino acid corresponding to position 1 in the Rs-AFP2 sequence), peptide 5 (N-terminal amino acid corresponding to position 17 in the Rs-AFP2 sequence) and peptide 10 (N-terminal amino acid corresponding to position 37 in the Rs-AFP2 sequence) have an IC50 value between 100 and 300 µg/mnl. Peptide 6 (N-terminal amino acid corresponding to position 21 in the Rs-AFP2 sequence), peptide 7 (N-terminal amino acid corresponding to position 25 in the Rs-AFP2 sequence), peptide 8 (N-terminal amino acid corresponding to position 29 in the Rs-AFP2 sequence) and peptide 9 (N-terrinal amino acid corresponding to position 33 in the Rs-AFP2 sequence) have an IC50 value less than 100 µg/ml.

EXAMPLE 6

Antifungal Activity of the Loop 1 Peptide Based on the Rs-AFP2 Protein

The Loop 1 peptide consists of ten amino acid residues and has the following sequence: CNYVFPAHKC. The two cysteines are cyclised. Table 8 shows the antifungal activity (as MIC values) of the Loop 1 peptide compared to the activity of the 15-mer Rs-AFP2-based peptides numbered 1 to 10. Table 9 shows the antifungal activity (as IC50 values) of the Loop I peptide compared to the activity of the most active 15-mer peptides. Activity was measured in ¹/₁₆ th PDB against F culmorum.

TABLE 8

| PEPTIDE | ANTIFUNGAL ACTIVITY, MIC µg/ml |
|---|---|
| 1 | 180 |
| 2 | >330 |
| 3 | 180 |
| 4 | 150 |
| 5 | 180 |
| 6 | 45 |
| 7 | 45 |
| 8 | 22.5 |
| 9 | 17.5 |
| 10 | 100 |
| Loop 1 | 2.5 |

TABLE 9

| PEPTIDE | ANTIFUNGAL ACTIVITY, IC50 (µg/ml) |
|---|---|
| 6 | 12 |
| 7 | 5 |
| 8 | 6 |
| 9 | 10 |
| Loop 1 | 4 |

EXAMPLE 7

Antifungal Activity of the 19-mer Peptides G1 and G2 Based on the Rs-AFP2 Protein and the 19-mer Peptide J1 Based on the Ah-AMP1 Protein Peptide G1 consisted of nineteen amino acid residues and had the sequence: ARHGSCNYVFPAHKCICYF. This peptide was conceived based on the observations that the most active 12-mer and 15-mer peptides fall within this stretch of amino acids and on the observation that this stretch of amino acids corresponds to a beta-strand/beta-turn/beta-strand region in the three dimensional model of Rs-AFP1 ( Fant F. et al (1994) Abstract of the 12th European Experimental NMR Conference, p247). Peptide G2 consisted of nineteen amino acid residues and had the sequence: ARHGSBNYVFPAHKBIBYF, where the symbol "B" represents an α lpha-aminobutyric acid residue. Peptide J1 consisted of nineteen amino acid residues and had the sequence: ASHGABHKRENHWKBFBYF where the symbol "B" represents an αlpha-aminobutyric acid residue.

Antifungal activity tests were carried out once in ½ PDB and once in ¹⁄₁₆ PDB. Table 10 gives the MIC and IC50 values.

TABLE 10

| | MEDIUM: 1/2 PDB | | MEDIUM: 1/16 PDB | |
|---|---|---|---|---|
| PEPTIDE | MIC (μg/ml) | IC50 (μg/ml) | MIC (μg/ml) | IC50 (μg/ml) |
| G1 | 25 | 19 | 12.5 | 10 |
| G2 | 25 | 17 | 12.5 | 10 |
| J1 | 12.5 | 9 | 6.25 | 5 |

The replacement of cysteine residues in G 1 by alpha-amino butyric acid to give peptide G2 does not affect antifungal activity. Peptide J1 was even more active than peptides G1 and G2.

EXAMPLE 8

Antifungal Activity of Combinations of Rs-AFP2 and the 15-mer Peptides

The 15-mer peptides were tested for their ability to affect the antifungal activity of the Rs-AFP2 protein. Each peptide was added at a sub-inhibitory concentration (20 μg/ml) to a twofold dilution series of Rs-AFP2 ranging from 20 μg/ml down to 0.15 μg/ml. In the control series only water was added. The target fungus was F culmorum and the growth medium was SMF. In order to exclude the effect of differential binding of the peptides to the microplate wells, the plates were coated with bovine serum albumin. Table 11 shows the relative specific antifungal activity of the Rs-AFP2/peptide combinations in comparison to the antifungal activity of Rs-AFP2. The relative specific activity is defined as one hundred times the MIC of Rs-AFP2 divided by the MIC of the Rs-AFP2/peptide combination. Data are based on duplicate tests.

TABLE 11

| peptide added | relative specific antifungal activity |
|---|---|
| – | 100 |
| 1 | 310 |
| 2 | 120 |
| 3 | 180 |
| 4 | 180 |
| 5 | 180 |
| 6 | 300 |
| 7 | 350 |
| 8 | 470 |
| 9 | 450 |
| 10 | 250 |

Except for peptide 2, presence of the peptides resulted in increased antifungal activity of Rs-AFP2. Peptides causing the strongest increase of the antifungal activity were 1, 6, 7, 8, 9 and (to a lesser extent) 10. These peptides potentiated the activity of Rs-AFP2 from 3 to 5-fold. When added to Rs-AFP1 in a similar assay, the peptides caused a comparable enhancement of the antifungal activity.

The antifungal activity tests show that in most cases the Rs-AFP/peptide combination has an increase in activity compared to the activity of Rs-AFP or the individual peptide when used alone. This increase in activity may be an enhancement due to synergistic interactions between the protein and peptide. For example, protein/peptide hetero-oligomers may be forming resulting in a complex with higher activity. Synergistic interactions between related but non-identical vertebrate antimicrobial peptides have been previously reported (Mor et al, 1994, J Biol Chem, 269, 31635–31641). Alternatively, the Rs-AFP protein and the synthetic peptides may have differing modes of action so that their simultaneous action at two distinct sites results in a synergistic antifungal effect.

EXAMPLE 9

Antifungal Activity of the 15-mer Peptides in the Presence of Inorganic Cations

In order to evaluate the sensitivity of the Rs-AFP2-derived 1 5-mer peptides to the presence of salts, different concentrations of a divalent ($Ca^{2+}$) and a monovalent ($K^+$) cation were added to the growth medium in the antifungal activity assay on F culmorum. Table 12 shows the results, expressed in MIC values for peptides 1 to 10 and for Rs-AFP2.

For peptides 1 to 5 and peptide 10, which have weaker antifungal activity in ½ PDB, the addition of salts at all concentrations tested caused a nearly complete loss of the antifungal activity. The addition of 10 mM KCl did not significantly affect the antifungal activity of the more active peptides 6 to 8. The active peptide 9 did, however, show a marked increase in its MIC value (from 30 to 250 μg/ml) although it was still more active than peptides 1 to 5 and 10. In the presence of 50 mM KCl, the MIC values of peptides 6 and 7 increased by twofold, whereas those of peptides 8 and 9 increased by about 16-fold and 8-fold, respectively. The addition A of CaC12 had a greater effect. When CaC12 was present in the growth medium at a concentration of 1 mM, most peptides lost their activity although peptides 6 and 7 still inhibited growth of the test fungus at 250 μg/ml. At 5 mM CaC12, none of the peptides was active at concentrations below 500 μg/ml.

TABLE 12

| | MIC | ½ PDB supplemented with: | | | | |
|---|---|---|---|---|---|---|
| peptide | (μg/ml) ½ PDB | 10 mM KCl | 50 mM KCl | 1 mM CaCl2 | 5 mM CaCl2 | 50 mM KCl; 1 mM CaCl2 |
| 1 | 250 | 500 | >500 | >500 | >500 | >500 |
| 2 | >500 | >500 | >500 | >500 | >500 | >500 |
| 3 | 250 | >500 | >500 | 500 | 500 | 500 |
| 4 | 125 | 500 | 500 | 500 | 500 | 500 |
| 5 | 250 | 500 | 500 | 500 | 500 | 500 |
| 6 | 60 | 60 | 125 | 250 | 500 | 250 |
| 7 | 60 | 60 | 125 | 250 | 500 | 500 |
| 8 | 30 | 60 | 500 | 500 | >500 | >500 |
| 9 | 30 | 250 | 250 | 500 | 500 | 500 |
| 10 | 250 | 500 | 500 | 500 | 500 | 500 |
| AFP2 | 3 | 3 | 3 | 6 | 6 | 6 |

EXAMPLE 10

Comparison of Linear Loop Peptides of Rs-AFP. Ah-AMP1 and Dm-AMP1 in Media ½ PDB, SMF+ pH5 and SMF+ pH7 (MPS peptides)

Several β2–β3 loop peptides of Rs-AFP, Ah-AMP1 and Dm-AMP1 were tested and compared in one experiment. In ½ PDB the various Rs-AFP peptides showed similar activities (Table 13).

Substituting the cysteine residues by alpha-aminobutyric acid resulted in reduced activities. The addition of an extra lysine residue at the N-terminus, corresponding to Lys30 in Rs-AFP decreased the influence of the higher ionic strength on the antifungal activity even further.

TABLE 13

Antifungal activity of linear β2–β3 loop peptides from Rs-AFP2, Ah-AMP1 and Dm-AMP1 in media ½ PDB, SMF + pH5 and SMF + pH7.

| CODE | | IC50(μg/ml) | | |
|---|---|---|---|---|
| PEPTIDE | SEQUENCE | ½ PDB | SMF + pH5 | SMF + pH7 |
| G1 Rs-AFP | ARHGSCNYVFPAHKCICYF | 17.6 ± 1.1 | 17.5 ± 2.3 | 12.5 ± 0.4 |
| G2 Rs-AFP | ARHGSBNYVFPAHKBIBYF | 16.0 ± 1.2 | 50.0 ± 6.0 | >400 |
| N1 Rs-AFP | KARHGSBNYVFPAHKBIBYF | 14.0 ± 6.2 | 27.0 ± 7.7 | 142.6 ± 13.6 |
| J1 Ah-AMP1 | ASHGABHKRENHWKBIBYF | 9.1 ± 0.6 | 47 ± 33 | 173.4 ± 0.2 |
| N5 Dm-AMP1 | AAHGABHVRNGKHMBFBYF | 8.0 ± 0.4 | 20.9 ± 1.8 | 24.2 ± 0.2 |
| Rs-AFP2 | | 3.3 ± 0.0 | 5.2 ± 1.2 | 6.1 ± 1.3 |

*Fusarium culmorum* (2 * 10⁴ spores/ml); duplo experiments;
B = alpha-aminobutyric acid In ½ PDB the Ah-AMP1 and Dm-AMP1 loop peptides showed an almost two-fold higher activity as compared to their Rs-AFP counterpart, i.e., G2. Furthermore, the influence of salts was less pronounced for Ah-AMP1 than for G2, whereas the activity of Dm-AMP1 was only slightly decreased, even in SMF+ pH7.

EXAMPLE 11

Antifungal Activity of Overlapping 13- to 20-mer Peptides from the Rs-AFP2 Primary Amino Acid sequence Ile26 to Phe49 in Media ½ PDB, SMF+ pH5 and SMF+ pH7 (MPS Peptides)

Figure 10A:
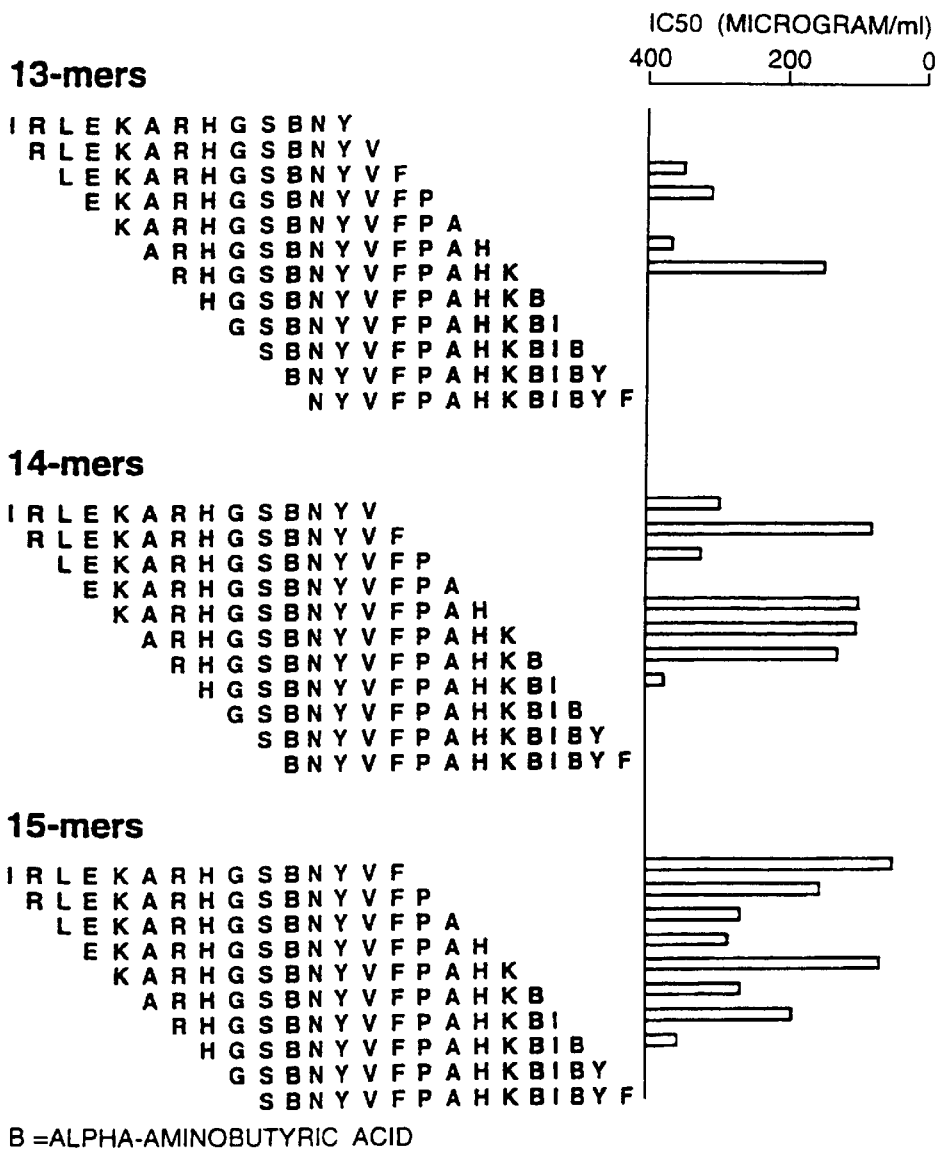
FIG. 10a is a diagram summarising active Rs-AFP2-based 13-mer, 14-mer and 15-mer peptides.
Figure 10B:
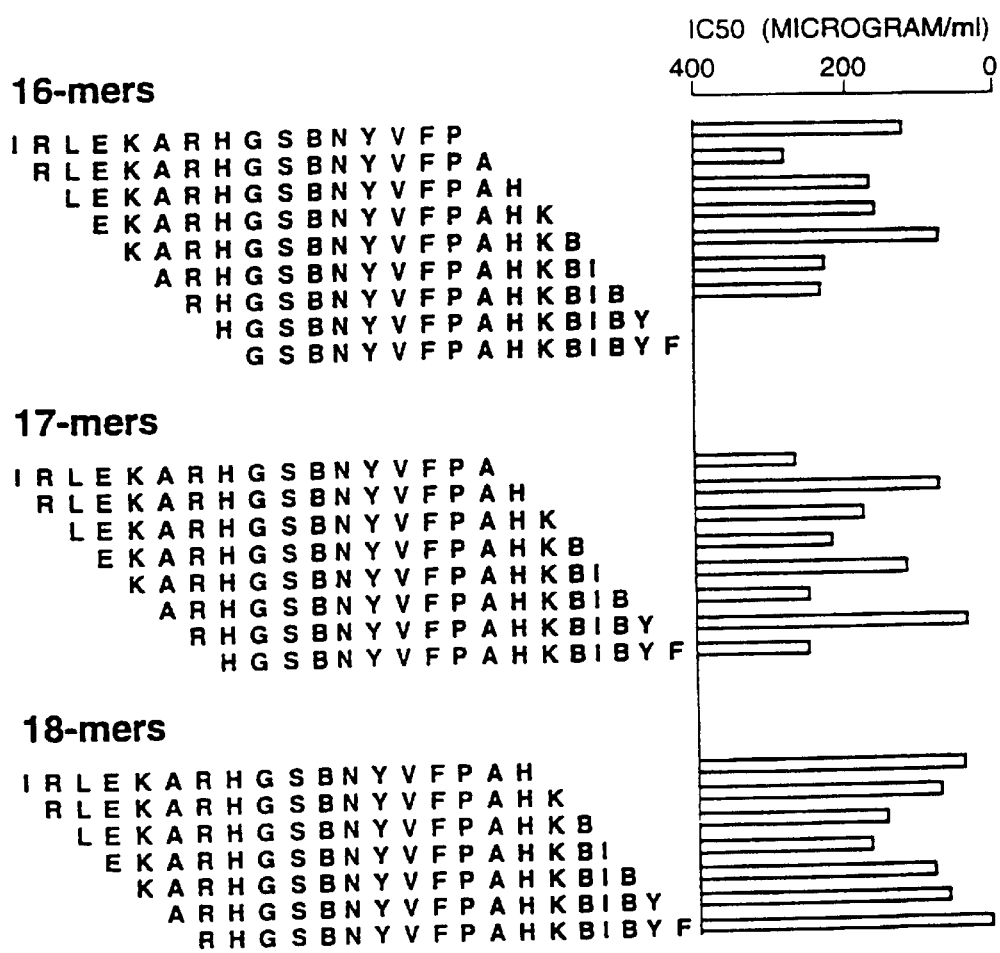
FIG. 10b is a diagram summarising active Rs-AFP2-based 16-mer, 17-mer and 18-mer peptides.
Figure 10C:
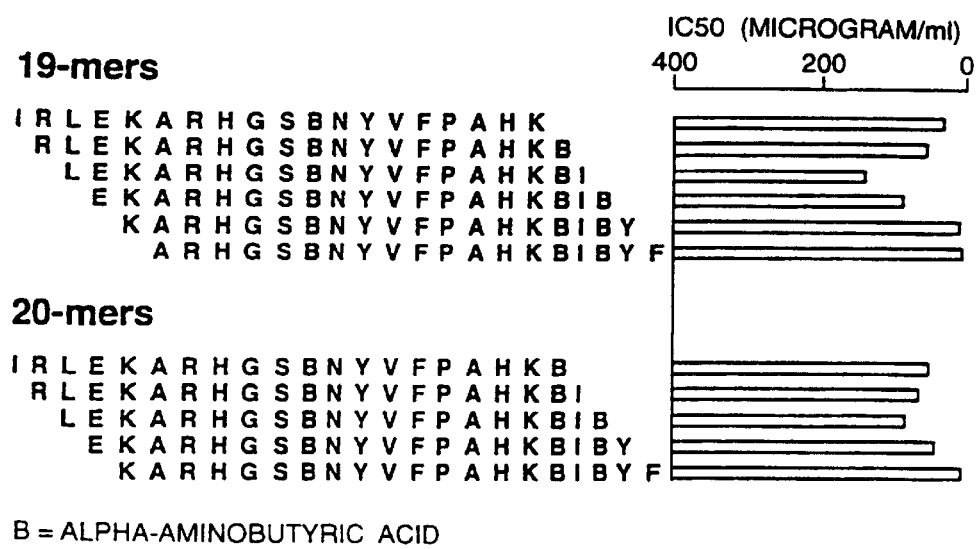
FIG. 10c is a diagram summarising active Rs-AFP2-based 19-mer and 20-mer peptides.

The most active region of Rs-AFP is located at the β2-strand/turn/β3-strand region. To inventory in more detail the contribution of the amino acids in this region to the antifungal activity a set of overlapping 13- to 20-mer peptides was synthesised and tested on *Fusarium culmorum*. In this set cysteine residues were replaced by alpha-aminobutyric acid. A graphical representation of the results with the overlapping 13- to 20-mer peptides is shown in FIG. 10a (13- to 15-mers), 10b (16- to 18-mers) and 10c (19- and 20-mers). In the set 13- and 14-mer peptides two activity areas can be seen: one around the His33-Gly34-Ser35 sequence and the other around Tyr38-Val39-Phe40. From the set of 15-mers onwards these activity areas turn to one activity region, although the IC50 values differ in relation to the size and composition of the particular peptides.

In FIGS. 11a and b all 13- to 20-mer peptides with the same N-terminal amino acid have been clustered. Clustering of all peptides with identical C-terminal residues can be seen in FIGS. 12a and 12b. The addition of a particular amino acid to the C— or N-terminal side, respectively, can turn a non-active peptide into a very active one, e.g., addition of Arg32 to the 16-mer His33-Tyr48. A summary of this evaluation is shown in FIG. 13. In the region Ile26 to Phe49 the 13- to 20-mer peptides from His33 onwards are less active. Similarly, peptides from Ile26 upto Val39 are less active. Minimal requirements for active peptides are the presence of Arg27 and Phe40, Lys30 and His43, or Arg32 and Lys44. Very active peptides start with Lys30, Ala31, Arg32 or His33 and end with Tyr48 or Phe49. In SMF+ pH5 and pH7 media the activity of the peptides was substantially reduced. However, as is shown in Table 14, some longer peptides do show activity even at higher ionic strength and increased pH value. Again, the presence of Phe49 and Ala31, Arg32, His33 is necessary. In medium ½ PDB these 18- to 20-mer peptides are only a factor 5 to 8 less potent than Rs-AFP2 when molar quantities are compared.

TABLE 14

Antifungal activity of Rs-AFP2 based 18-, 19- and 20-mer peptides with Phe49 as the C-terminal residue in media ½ PDB, SMF + pH5 and SMF + pH7.

| CODE/ | | IC50(μg/ml) | | |
|---|---|---|---|---|
| PEPTIDE | SEQUENCE | ½ PDB | SMF + pH5 | SMF + pH7 |
| P02 18-mer | RHGSBNYVFPAHKBIBYF | 8.9 | 69 ± 34 | 133 ± 6 |
| O01 19-mer | ARHGSBNYVFPAHKBIBYF | 5.6 | 102 ± 2 | 159 ± 5 |
| Q06 20-mer | KARHGSBNYVFPAHKBIBYF | 4.8 | 31 ± 17 | 62 ± 8 |
| Rs-AFP2 | | 2.5 ± 0.8 | 7.2 ± 0.6 | 3.7 ± 0.6 |

*Fusarium culmorum* (2 * 10⁴ spores/ml); duplo experiments, except for ½ PDB, in the first experiment the peptides were diluted up to 12.5 μg/ml, a dilution that appeared to be insufficient to score the IC50 value.
B = alpha-aminobutyric acid.

What is claimed is:

1. An antifungal peptide consisting of at least six amino acid residues identical to a run of amino acid residues found between position 21 and 51 of SEQ ID NO: 35.

2. An antifungal peptide according to claim 1 wherein said peptide comprises an arginine residue at position 27 and a phenylalanine residue at position 40; a lysine residue at position 30 and a histidine residue at position 43 or an arginine residue at position 32 and a lysine residue at position 44.

3. An antifungal composition comprising a peptide as claimed in claim 1.

4. An antifungal composition according to claim 3 additionally comprising Rs-AFP1 (SEQ ID NO: 34) or Rs-AFP2 (SEQ ID NO: 35).

5. A process of combating fungi or bacteria which comprises exposing them to a peptide as claimed in claim 1.

6. A process of combating fungi or bacteria which comprises exposing them to a composition as claimed in claim 3.

7. The antifungal peptide according to claim 1 wherein the N-terminus of said peptide consists of the lysine at position 30; or the alanine at position 31; or the arginine at position 32; or the histidine at position 33 of the sequence depicted as SEQ ID NO: 35 and the C-terminus of said peptide consists of the tyrosine at position 48 or the phenylalanine at position 49 of the sequence depicted as SEQ ID NO: 35.

8. The antifungal peptide of claim 1 consisting of a sequence selected from the group consisting of SEQ ID NOS: 1 to 22.

* * * * *

SEQUENCE LISTING

<160> NUMBER OF SEQ ID NOS: 141

<210> SEQ ID NO 1
<211> LENGTH: 15
<212> TYPE: PRT
<213> ORGANISM: Raphanus sativus

<400> SEQUENCE: 1

Cys Lys Asn Gln Cys Ile Arg Leu Glu Lys Ala Arg His Gly Ser
 1               5                  10                  15

-continued

```
<210> SEQ ID NO 2
<211> LENGTH: 15
<212> TYPE: PRT
<213> ORGANISM: Raphanus sativus

<400> SEQUENCE: 2

Cys Ile Arg Leu Glu Lys Ala Arg His Gly Ser Cys Asn Tyr Val
 1               5                  10                  15

<210> SEQ ID NO 3
<211> LENGTH: 15
<212> TYPE: PRT
<213> ORGANISM: Raphanus sativus

<400> SEQUENCE: 3

Glu Lys Ala Arg His Gly Ser Cys Asn Tyr Val Phe Pro Ala His
 1               5                  10                  15

<210> SEQ ID NO 4
<211> LENGTH: 15
<212> TYPE: PRT
<213> ORGANISM: Raphanus sativus

<400> SEQUENCE: 4

His Gly Ser Cys Asn Tyr Val Phe Pro Ala His Lys Cys Ile Cys
 1               5                  10                  15

<210> SEQ ID NO 5
<211> LENGTH: 10
<212> TYPE: PRT
<213> ORGANISM: Raphanus sativus

<400> SEQUENCE: 5

Cys Asn Tyr Val Phe Pro Ala His Lys Cys
 1               5                  10

<210> SEQ ID NO 6
<211> LENGTH: 6
<212> TYPE: PRT
<213> ORGANISM: Raphanus sativus

<400> SEQUENCE: 6

Phe Pro Ala His Lys Cys
 1               5

<210> SEQ ID NO 7
<211> LENGTH: 6
<212> TYPE: PRT
<213> ORGANISM: Raphanus sativus

<400> SEQUENCE: 7

Ala His Lys Cys Ile Cys
 1               5

<210> SEQ ID NO 8
<211> LENGTH: 6
<212> TYPE: PRT
<213> ORGANISM: Raphanus sativus

<400> SEQUENCE: 8

His Lys Cys Ile Cys Tyr
 1               5

<210> SEQ ID NO 9
<211> LENGTH: 9
```

-continued

```
<212> TYPE: PRT
<213> ORGANISM: Raphanus sativus

<400> SEQUENCE: 9

Gln Cys Ile Arg Leu Glu Lys Ala Arg
  1               5

<210> SEQ ID NO 10
<211> LENGTH: 9
<212> TYPE: PRT
<213> ORGANISM: Raphanus sativus

<400> SEQUENCE: 10

Cys Ile Arg Leu Glu Lys Ala Arg His
  1               5

<210> SEQ ID NO 11
<211> LENGTH: 9
<212> TYPE: PRT
<213> ORGANISM: Raphanus sativus

<400> SEQUENCE: 11

Arg His Gly Ser Cys Asn Tyr Val Phe
  1               5

<210> SEQ ID NO 12
<211> LENGTH: 9
<212> TYPE: PRT
<213> ORGANISM: Raphanus sativus

<400> SEQUENCE: 12

Cys Asn Tyr Val Phe Pro Ala His Lys
  1               5

<210> SEQ ID NO 13
<211> LENGTH: 9
<212> TYPE: PRT
<213> ORGANISM: Raphanus sativus

<400> SEQUENCE: 13

Phe Pro Ala His Lys Cys Ile Cys Tyr
  1               5

<210> SEQ ID NO 14
<211> LENGTH: 9
<212> TYPE: PRT
<213> ORGANISM: Raphanus sativus

<400> SEQUENCE: 14

Pro Ala His Lys Cys Ile Cys Tyr Phe
  1               5

<210> SEQ ID NO 15
<211> LENGTH: 9
<212> TYPE: PRT
<213> ORGANISM: Raphanus sativus

<400> SEQUENCE: 15

Ala His Lys Cys Ile Cys Tyr Phe Pro
  1               5

<210> SEQ ID NO 16
<211> LENGTH: 9
<212> TYPE: PRT
<213> ORGANISM: Raphanus sativus
```

<400> SEQUENCE: 16

His Lys Cys Ile Cys Tyr Phe Pro Cys
 1               5

<210> SEQ ID NO 17
<211> LENGTH: 12
<212> TYPE: PRT
<213> ORGANISM: Raphanus sativus

<400> SEQUENCE: 17

Cys Ile Arg Leu Glu Lys Ala Arg His Gly Ser Cys
 1               5                  10

<210> SEQ ID NO 18
<211> LENGTH: 12
<212> TYPE: PRT
<213> ORGANISM: Raphanus sativus

<400> SEQUENCE: 18

Glu Lys Ala Arg His Gly Ser Cys Asn Tyr Val Phe
 1               5                  10

<210> SEQ ID NO 19
<211> LENGTH: 12
<212> TYPE: PRT
<213> ORGANISM: Raphanus sativus

<400> SEQUENCE: 19

Lys Ala Arg His Gly Ser Cys Asn Tyr Val Phe Pro
 1               5                  10

<210> SEQ ID NO 20
<211> LENGTH: 12
<212> TYPE: PRT
<213> ORGANISM: Raphanus sativus

<400> SEQUENCE: 20

Arg His Gly Ser Cys Asn Tyr Val Phe Pro Ala His
 1               5                  10

<210> SEQ ID NO 21
<211> LENGTH: 12
<212> TYPE: PRT
<213> ORGANISM: Raphanus sativus

<400> SEQUENCE: 21

His Gly Ser Cys Asn Tyr Val Phe Pro Ala His Lys
 1               5                  10

<210> SEQ ID NO 22
<211> LENGTH: 19
<212> TYPE: PRT
<213> ORGANISM: Raphanus sativus

<400> SEQUENCE: 22

Ala Arg His Gly Ser Cys Asn Tyr Val Phe Pro Ala His Lys Cys Ile
 1               5                  10                  15

Cys Tyr Phe

<210> SEQ ID NO 23
<211> LENGTH: 19
<212> TYPE: PRT
<213> ORGANISM: Aesculus hippocastanum

<400> SEQUENCE: 23

Ala Ser His Gly Ala Cys His Lys Arg Glu Asn His Trp Lys Cys Phe
1               5                   10                  15

Cys Tyr Phe

<210> SEQ ID NO 24
<211> LENGTH: 19
<212> TYPE: PRT
<213> ORGANISM: Dahlia merckii

<400> SEQUENCE: 24

Ala Ala His Gly Ala Cys His Val Arg Asn Gly Lys His Met Cys Phe
1               5                   10                  15

Cys Tyr Phe

<210> SEQ ID NO 25
<211> LENGTH: 19
<212> TYPE: PRT
<213> ORGANISM: Raphanus sativus

<400> SEQUENCE: 25

Ala Arg His Gly Ser Cys Asn Tyr Val Phe Pro Ala His Lys Cys Ile
1               5                   10                  15

Cys Tyr Phe

<210> SEQ ID NO 26
<211> LENGTH: 19
<212> TYPE: PRT
<213> ORGANISM: Raphanus sativus
<220> FEATURE:
<221> NAME/KEY: MOD_RES
<222> LOCATION: 6
<223> OTHER INFORMATION: Abu
<221> NAME/KEY: MOD_RES
<222> LOCATION: 15
<223> OTHER INFORMATION: Abu
<221> NAME/KEY: MOD_RES
<222> LOCATION: 17
<223> OTHER INFORMATION: Abu

<400> SEQUENCE: 26

Ala Arg His Gly Ser Cys Asn Tyr Val Phe Pro Ala His Lys Cys Ile
1               5                   10                  15

Cys Tyr Phe

<210> SEQ ID NO 27
<211> LENGTH: 19
<212> TYPE: PRT
<213> ORGANISM: Aesculus hippocastanum
<220> FEATURE:
<221> NAME/KEY: MOD_RES
<222> LOCATION: 6
<223> OTHER INFORMATION: Abu
<221> NAME/KEY: MOD_RES
<222> LOCATION: 15
<223> OTHER INFORMATION: Abu
<221> NAME/KEY: MOD_RES
<222> LOCATION: 17
<223> OTHER INFORMATION: Abu

<400> SEQUENCE: 27

Ala Ser His Gly Ala Cys His Lys Arg Glu Asn His Trp Lys Cys Phe
1               5                   10                  15

Cys Tyr Phe

<210> SEQ ID NO 28
<211> LENGTH: 10
<212> TYPE: PRT
<213> ORGANISM: Raphanus sativus

<400> SEQUENCE: 28

Cys Asn Tyr Val Phe Pro Ala His Lys Cys
 1               5                  10

<210> SEQ ID NO 29
<211> LENGTH: 20
<212> TYPE: PRT
<213> ORGANISM: Raphanus sativus
<220> FEATURE:
<221> NAME/KEY: MOD_RES
<222> LOCATION: 7
<223> OTHER INFORMATION: Abu
<221> NAME/KEY: MOD_RES
<222> LOCATION: 16
<223> OTHER INFORMATION: Abu
<221> NAME/KEY: MOD_RES
<222> LOCATION: 18
<223> OTHER INFORMATION: Abu

<400> SEQUENCE: 29

Lys Ala Arg His Gly Ser Cys Asn Tyr Val Phe Pro Ala His Lys Cys
 1               5                  10                  15

Ile Cys Tyr Phe
            20

<210> SEQ ID NO 30
<211> LENGTH: 19
<212> TYPE: PRT
<213> ORGANISM: Dahlia merckii
<220> FEATURE:
<221> NAME/KEY: MOD_RES
<222> LOCATION: 6
<223> OTHER INFORMATION: Abu
<221> NAME/KEY: MOD_RES
<222> LOCATION: 15
<223> OTHER INFORMATION: Abu
<221> NAME/KEY: MOD_RES
<222> LOCATION: 17
<223> OTHER INFORMATION: Abu

<400> SEQUENCE: 30

Ala Ala His Gly Ala Cys His Val Arg Asn Gly Lys His Met Cys Phe
 1               5                  10                  15

Cys Tyr Phe

<210> SEQ ID NO 31
<211> LENGTH: 18
<212> TYPE: PRT
<213> ORGANISM: Raphanus sativus
<220> FEATURE:
<221> NAME/KEY: MOD_RES
<222> LOCATION: 5
<223> OTHER INFORMATION: Abu
<221> NAME/KEY: MOD_RES
<222> LOCATION: 14
<223> OTHER INFORMATION: Abu
<221> NAME/KEY: MOD_RES
<222> LOCATION: 16
<223> OTHER INFORMATION: Abu

<400> SEQUENCE: 31

Arg His Gly Ser Cys Asn Tyr Val Phe Pro Ala His Lys Cys Ile Cys
 1               5                  10                  15

Tyr Phe

<210> SEQ ID NO 32
<211> LENGTH: 19
<212> TYPE: PRT
<213> ORGANISM: Raphanus sativus
<220> FEATURE:
<221> NAME/KEY: MOD_RES
<222> LOCATION: 6
<223> OTHER INFORMATION: Abu
<221> NAME/KEY: MOD_RES
<222> LOCATION: 15
<223> OTHER INFORMATION: Abu
<221> NAME/KEY: MOD_RES
<222> LOCATION: 17
<223> OTHER INFORMATION: Abu

<400> SEQUENCE: 32

Ala Arg His Gly Ser Cys Asn Tyr Val Phe Pro Ala His Lys Cys Ile
 1               5                  10                  15

Cys Tyr Phe

<210> SEQ ID NO 33
<211> LENGTH: 20
<212> TYPE: PRT
<213> ORGANISM: Raphanus sativus
<220> FEATURE:
<221> NAME/KEY: MOD_RES
<222> LOCATION: 7
<223> OTHER INFORMATION: Abu
<221> NAME/KEY: MOD_RES
<222> LOCATION: 16
<223> OTHER INFORMATION: Abu
<221> NAME/KEY: MOD_RES
<222> LOCATION: 18
<223> OTHER INFORMATION: Abu

<400> SEQUENCE: 33

Lys Ala Arg His Gly Ser Cys Asn Tyr Val Phe Pro Ala His Lys Cys
 1               5                  10                  15

Ile Cys Tyr Phe
            20

<210> SEQ ID NO 34
<211> LENGTH: 51
<212> TYPE: PRT
<213> ORGANISM: Raphanus sativus

<400> SEQUENCE: 34

Gln Lys Leu Cys Glu Arg Pro Ser Gly Thr Trp Ser Gly Val Cys Gly
 1               5                  10                  15

Asn Asn Asn Ala Cys Lys Asn Gln Cys Ile Asn Leu Glu Lys Ala Arg
                20                  25                  30

His Gly Ser Cys Asn Tyr Val Phe Pro Ala His Lys Cys Ile Cys Tyr
            35                  40                  45

Phe Pro Cys
        50

<210> SEQ ID NO 35
<211> LENGTH: 51
<212> TYPE: PRT
<213> ORGANISM: Raphanus sativus

<400> SEQUENCE: 35

Gln Lys Leu Cys Gln Arg Pro Ser Gly Thr Trp Ser Gly Val Cys Gly

-continued

```
                1               5                   10                  15
Asn Asn Asn Ala Cys Lys Asn Gln Cys Ile Arg Leu Glu Lys Ala Arg
                    20                  25                  30

His Gly Ser Cys Asn Tyr Val Phe Pro Ala His Lys Cys Ile Cys Tyr
            35                  40                  45

Phe Pro Cys
    50
```

<210> SEQ ID NO 36
<211> LENGTH: 50
<212> TYPE: PRT
<213> ORGANISM: Raphanus sativus

<400> SEQUENCE: 36

```
Lys Leu Cys Glu Arg Ser Ser Gly Thr Trp Ser Gly Val Cys Gly Asn
1               5                   10                  15

Asn Asn Ala Cys Lys Asn Gln Cys Ile Arg Leu Glu Gly Ala Gln His
                    20                  25                  30

Gly Ser Cys Asn Tyr Val Phe Pro Ala His Lys Cys Ile Cys Tyr Phe
            35                  40                  45

Pro Cys
    50
```

<210> SEQ ID NO 37
<211> LENGTH: 51
<212> TYPE: PRT
<213> ORGANISM: Raphanus sativus

<400> SEQUENCE: 37

```
Gln Lys Leu Cys Glu Arg Ser Ser Gly Thr Trp Ser Gly Val Cys Gly
1               5                   10                  15

Asn Asn Asn Ala Cys Lys Asn Gln Cys Ile Asn Leu Glu Gly Ala Arg
                    20                  25                  30

His Gly Ser Cys Asn Tyr Ile Phe Pro Tyr His Arg Cys Ile Cys Tyr
            35                  40                  45

Phe Pro Cys
    50
```

<210> SEQ ID NO 38
<211> LENGTH: 27
<212> TYPE: PRT
<213> ORGANISM: Brassica rapa

<400> SEQUENCE: 38

```
Gln Lys Leu Cys Glu Arg Pro Ser Gly Thr Trp Ser Gly Val Cys Gly
1               5                   10                  15

Asn Asn Asn Ala Cys Lys Asn Gln Cys Ile Asn
                    20                  25
```

<210> SEQ ID NO 39
<211> LENGTH: 27
<212> TYPE: PRT
<213> ORGANISM: Brassica rapa
<220> FEATURE:
<221> NAME/KEY: VARIANT
<222> LOCATION: 11
<223> OTHER INFORMATION: Xaa = Any Amino Acid and post-translationally
      modified standard amino acids

<400> SEQUENCE: 39

Gln Lys Leu Cys Glu Arg Pro Ser Gly Thr Xaa Ser Gly Val Cys Gly

```
1               5                   10                  15
Asn Asn Asn Ala Cys Lys Asn Gln Cys Ile Arg
            20                  25

<210> SEQ ID NO 40
<211> LENGTH: 30
<212> TYPE: PRT
<213> ORGANISM: Brassica napus

<400> SEQUENCE: 40

Gln Lys Leu Cys Glu Arg Pro Ser Gly Thr Trp Ser Gly Val Cys Gly
  1               5                   10                  15
Asn Asn Asn Ala Cys Lys Asn Gln Cys Ile Asn Leu Glu Lys
            20                  25                  30

<210> SEQ ID NO 41
<211> LENGTH: 23
<212> TYPE: PRT
<213> ORGANISM: Brassica napus

<400> SEQUENCE: 41

Gln Lys Leu Cys Glu Arg Pro Ser Gly Thr Trp Ser Gly Val Cys Gly
  1               5                   10                  15
Asn Asn Asn Ala Cys Lys Asn
            20

<210> SEQ ID NO 42
<211> LENGTH: 25
<212> TYPE: PRT
<213> ORGANISM: Sinapis alba

<400> SEQUENCE: 42

Gln Lys Leu Cys Glu Arg Pro Ser Gly Thr Trp Ser Gly Val Cys Gly
  1               5                   10                  15
Asn Asn Asn Ala Cys Lys Asn Gln Cys
            20                  25

<210> SEQ ID NO 43
<211> LENGTH: 26
<212> TYPE: PRT
<213> ORGANISM: Sinapis alba

<400> SEQUENCE: 43

Gln Lys Leu Cys Gln Arg Pro Ser Gly Thr Trp Ser Gly Val Cys Gly
  1               5                   10                  15
Asn Asn Asn Ala Cys Arg Asn Gln Cys Ile
            20                  25

<210> SEQ ID NO 44
<211> LENGTH: 27
<212> TYPE: PRT
<213> ORGANISM: Arabidopsis thaliana

<400> SEQUENCE: 44

Gln Lys Leu Cys Glu Arg Pro Ser Gly Thr Trp Ser Gly Val Cys Gly
  1               5                   10                  15
Asn Ser Asn Ala Cys Lys Asn Gln Cys Ile Asn
            20                  25

<210> SEQ ID NO 45
<211> LENGTH: 414
<212> TYPE: DNA
<213> ORGANISM: Raphanus sativus
```

<400> SEQUENCE: 45

```
gttttattag tgatcatggc taagtttgcg tccatcatcg cacttctttt tgctgctctt      60
gttcttttg  ctgctttcga agcaccaaca atggtggaag cacagaagtt gtgcgaaagg     120
ccaagtggga catggtcagg agtctgtgga acaataacg  catgcaagaa tcagtgcatt     180
aaccttgaga aagcacgaca tggatcttgc aactatgtct tcccagctca caagtgtatc     240
tgctactttc cttgttaatt tatcgcaaac tctttggtga atagtttta  tgtaatttac     300
acaaaataag tcagtgtcac tatccatgag tgattttaag acatgtacca gatatgttat    360
gttggttcgg ttatacaaat aaagttttat tcaccaaaaa aaaaaaaaaa aaaa           414
```

<210> SEQ ID NO 46
<211> LENGTH: 15
<212> TYPE: PRT
<213> ORGANISM: Raphanus sativus

<400> SEQUENCE: 46

Gln Lys Leu Cys Gln Arg Pro Ser Gly Thr Trp Ser Gly Val Cys
1               5                   10                  15

<210> SEQ ID NO 47
<211> LENGTH: 15
<212> TYPE: PRT
<213> ORGANISM: Raphanus sativus

<400> SEQUENCE: 47

Gln Arg Pro Ser Gly Thr Trp Ser Gly Val Cys Gly Asn Asn Asn
1               5                   10                  15

<210> SEQ ID NO 48
<211> LENGTH: 15
<212> TYPE: PRT
<213> ORGANISM: Raphanus sativus

<400> SEQUENCE: 48

Gly Thr Trp Ser Gly Val Cys Gly Asn Asn Asn Ala Cys Lys Asn
1               5                   10                  15

<210> SEQ ID NO 49
<211> LENGTH: 15
<212> TYPE: PRT
<213> ORGANISM: Raphanus sativus

<400> SEQUENCE: 49

Gly Val Cys Gly Asn Asn Asn Ala Cys Lys Asn Gln Cys Ile Arg
1               5                   10                  15

<210> SEQ ID NO 50
<211> LENGTH: 15
<212> TYPE: PRT
<213> ORGANISM: Raphanus sativus

<400> SEQUENCE: 50

Asn Asn Asn Ala Cys Lys Asn Gln Cys Ile Arg Leu Glu Lys Ala
1               5                   10                  15

<210> SEQ ID NO 51
<211> LENGTH: 15
<212> TYPE: PRT
<213> ORGANISM: Raphanus sativus

<400> SEQUENCE: 51

Cys Lys Asn Gln Cys Ile Arg Leu Glu Lys Ala Arg His Gly Ser
1               5                   10                  15

<210> SEQ ID NO 52
<211> LENGTH: 15
<212> TYPE: PRT
<213> ORGANISM: Raphanus sativus

<400> SEQUENCE: 52

Cys Ile Arg Leu Glu Lys Ala Arg His Gly Ser Cys Asn Tyr Val
1               5                   10                  15

<210> SEQ ID NO 53
<211> LENGTH: 15
<212> TYPE: PRT
<213> ORGANISM: Raphanus sativus

<400> SEQUENCE: 53

Glu Lys Ala Arg His Gly Ser Cys Asn Tyr Val Phe Pro Ala His
1               5                   10                  15

<210> SEQ ID NO 54
<211> LENGTH: 15
<212> TYPE: PRT
<213> ORGANISM: Raphanus sativus

<400> SEQUENCE: 54

His Gly Ser Cys Asn Tyr Val Phe Pro Ala His Lys Cys Ile Cys
1               5                   10                  15

<210> SEQ ID NO 55
<211> LENGTH: 15
<212> TYPE: PRT
<213> ORGANISM: Raphanus sativus

<400> SEQUENCE: 55

Asn Tyr Val Phe Pro Ala His Lys Cys Ile Cys Tyr Phe Pro Cys
1               5                   10                  15

<210> SEQ ID NO 56
<211> LENGTH: 54
<212> TYPE: PRT
<213> ORGANISM: Huechera sanguinea

<400> SEQUENCE: 56

Asp Gly Val Lys Leu Cys Asp Val Pro Ser Gly Thr Trp Ser Gly His
1               5                   10                  15

Cys Gly Ser Ser Ser Lys Cys Ser Gln Gln Cys Lys Asp Arg Glu His
                20                  25                  30

Phe Ala Tyr Gly Gly Ala Cys His Tyr Gln Phe Pro Ser Val Lys Cys
            35                  40                  45

Phe Cys Lys Arg Gln Cys
            50

<210> SEQ ID NO 57
<211> LENGTH: 50
<212> TYPE: PRT
<213> ORGANISM: Aesculus hippocastanum

<400> SEQUENCE: 57

Leu Cys Asn Glu Arg Pro Ser Gln Thr Trp Ser Gly Asn Cys Gly Asn
1               5                   10                  15

-continued

Thr Ala His Cys Asp Lys Gln Cys Gln Asp Trp Glu Lys Ala Ser His
            20                  25                  30

Gly Ala Cys His Lys Arg Glu Asn His Trp Lys Cys Phe Cys Tyr Phe
            35                  40                  45

Asn Cys
    50

<210> SEQ ID NO 58
<211> LENGTH: 50
<212> TYPE: PRT
<213> ORGANISM: Dahlia merckii

<400> SEQUENCE: 58

Glu Leu Cys Glu Lys Ala Ser Lys Thr Trp Ser Gly Asn Cys Gly Asn
 1               5                  10                  15

Thr Gly His Cys Asp Asn Gln Cys Lys Ser Trp Glu Gly Ala Ala His
            20                  25                  30

Gly Ala Cys His Val Arg Asn Gly Lys His Met Cys Phe Cys Tyr Phe
            35                  40                  45

Asn Cys
    50

<210> SEQ ID NO 59
<211> LENGTH: 13
<212> TYPE: PRT
<213> ORGANISM: Raphanus sativus
<220> FEATURE:
<221> NAME/KEY: MOD_RES
<222> LOCATION: 11
<223> OTHER INFORMATION: Abu

<400> SEQUENCE: 59

Ile Arg Leu Glu Lys Ala Arg His Gly Ser Cys Asn Tyr
 1               5                  10

<210> SEQ ID NO 60
<211> LENGTH: 13
<212> TYPE: PRT
<213> ORGANISM: Raphanus sativus
<220> FEATURE:
<221> NAME/KEY: MOD_RES
<222> LOCATION: 10
<223> OTHER INFORMATION: Abu

<400> SEQUENCE: 60

Arg Leu Glu Lys Ala Arg His Gly Ser Cys Asn Tyr Val
 1               5                  10

<210> SEQ ID NO 61
<211> LENGTH: 13
<212> TYPE: PRT
<213> ORGANISM: Raphanus sativus
<220> FEATURE:
<221> NAME/KEY: MOD_RES
<222> LOCATION: 9
<223> OTHER INFORMATION: Abu

<400> SEQUENCE: 61

Leu Glu Lys Ala Arg His Gly Ser Cys Asn Tyr Val Phe
 1               5                  10

<210> SEQ ID NO 62
<211> LENGTH: 13
<212> TYPE: PRT
<213> ORGANISM: Raphanus sativus

```
<220> FEATURE:
<221> NAME/KEY: MOD_RES
<222> LOCATION: 8
<223> OTHER INFORMATION: Abu

<400> SEQUENCE: 62

Glu Lys Ala Arg His Gly Ser Cys Asn Tyr Val Phe Pro
 1               5                  10

<210> SEQ ID NO 63
<211> LENGTH: 13
<212> TYPE: PRT
<213> ORGANISM: Raphanus sativus
<220> FEATURE:
<221> NAME/KEY: MOD_RES
<222> LOCATION: 7
<223> OTHER INFORMATION: Abu

<400> SEQUENCE: 63

Lys Ala Arg His Gly Ser Cys Asn Tyr Val Phe Pro Ala
 1               5                  10

<210> SEQ ID NO 64
<211> LENGTH: 13
<212> TYPE: PRT
<213> ORGANISM: Raphanus sativus
<220> FEATURE:
<221> NAME/KEY: MOD_RES
<222> LOCATION: 6
<223> OTHER INFORMATION: Abu

<400> SEQUENCE: 64

Ala Arg His Gly Ser Cys Asn Tyr Val Phe Pro Ala His
 1               5                  10

<210> SEQ ID NO 65
<211> LENGTH: 13
<212> TYPE: PRT
<213> ORGANISM: Raphanus sativus
<220> FEATURE:
<221> NAME/KEY: MOD_RES
<222> LOCATION: 5
<223> OTHER INFORMATION: Abu

<400> SEQUENCE: 65

Arg His Gly Ser Cys Asn Tyr Val Phe Pro Ala His Lys
 1               5                  10

<210> SEQ ID NO 66
<211> LENGTH: 13
<212> TYPE: PRT
<213> ORGANISM: Raphanus sativus
<220> FEATURE:
<221> NAME/KEY: MOD_RES
<222> LOCATION: 4
<223> OTHER INFORMATION: Abu
<221> NAME/KEY: MOD_RES
<222> LOCATION: 13
<223> OTHER INFORMATION: Abu

<400> SEQUENCE: 66

His Gly Ser Cys Asn Tyr Val Phe Pro Ala His Lys Cys
 1               5                  10

<210> SEQ ID NO 67
<211> LENGTH: 13
<212> TYPE: PRT
<213> ORGANISM: Raphanus sativus
<220> FEATURE:
```

```
<221> NAME/KEY: MOD_RES
<222> LOCATION: 3
<223> OTHER INFORMATION: Abu
<221> NAME/KEY: MOD_RES
<222> LOCATION: 12
<223> OTHER INFORMATION: Abu

<400> SEQUENCE: 67

Gly Ser Cys Asn Tyr Val Phe Pro Ala His Lys Cys Ile
 1               5                  10

<210> SEQ ID NO 68
<211> LENGTH: 13
<212> TYPE: PRT
<213> ORGANISM: Raphanus sativus
<220> FEATURE:
<221> NAME/KEY: MOD_RES
<222> LOCATION: 2
<223> OTHER INFORMATION: Abu
<221> NAME/KEY: MOD_RES
<222> LOCATION: 11
<223> OTHER INFORMATION: Abu
<221> NAME/KEY: MOD_RES
<222> LOCATION: 13
<223> OTHER INFORMATION: Abu

<400> SEQUENCE: 68

Ser Cys Asn Tyr Val Phe Pro Ala His Lys Cys Ile Cys
 1               5                  10

<210> SEQ ID NO 69
<211> LENGTH: 13
<212> TYPE: PRT
<213> ORGANISM: Raphanus sativus
<220> FEATURE:
<221> NAME/KEY: MOD_RES
<222> LOCATION: 1
<223> OTHER INFORMATION: Abu
<221> NAME/KEY: MOD_RES
<222> LOCATION: 10
<223> OTHER INFORMATION: Abu
<221> NAME/KEY: MOD_RES
<222> LOCATION: 12
<223> OTHER INFORMATION: Abu

<400> SEQUENCE: 69

Cys Asn Tyr Val Phe Pro Ala His Lys Cys Ile Cys Tyr
 1               5                  10

<210> SEQ ID NO 70
<211> LENGTH: 13
<212> TYPE: PRT
<213> ORGANISM: Raphanus sativus
<220> FEATURE:
<221> NAME/KEY: MOD_RES
<222> LOCATION: 9
<223> OTHER INFORMATION: Abu
<221> NAME/KEY: MOD_RES
<222> LOCATION: 11
<223> OTHER INFORMATION: Abu

<400> SEQUENCE: 70

Asn Tyr Val Phe Pro Ala His Lys Cys Ile Cys Tyr Phe
 1               5                  10

<210> SEQ ID NO 71
<211> LENGTH: 14
<212> TYPE: PRT
<213> ORGANISM: Raphanus sativus
<220> FEATURE:
<221> NAME/KEY: MOD_RES
```

<222> LOCATION: 11
<223> OTHER INFORMATION: Abu

<400> SEQUENCE: 71

Ile Arg Leu Glu Lys Ala Arg His Gly Ser Cys Asn Tyr Val
1               5                   10

<210> SEQ ID NO 72
<211> LENGTH: 14
<212> TYPE: PRT
<213> ORGANISM: Raphanus sativus
<220> FEATURE:
<221> NAME/KEY: MOD_RES
<222> LOCATION: 10
<223> OTHER INFORMATION: Abu

<400> SEQUENCE: 72

Arg Leu Glu Lys Ala Arg His Gly Ser Cys Asn Tyr Val Phe
1               5                   10

<210> SEQ ID NO 73
<211> LENGTH: 14
<212> TYPE: PRT
<213> ORGANISM: Raphanus sativus
<220> FEATURE:
<221> NAME/KEY: MOD_RES
<222> LOCATION: 9
<223> OTHER INFORMATION: Abu

<400> SEQUENCE: 73

Leu Glu Lys Ala Arg His Gly Ser Cys Asn Tyr Val Phe Pro
1               5                   10

<210> SEQ ID NO 74
<211> LENGTH: 14
<212> TYPE: PRT
<213> ORGANISM: Raphanus sativus
<220> FEATURE:
<221> NAME/KEY: MOD_RES
<222> LOCATION: 8
<223> OTHER INFORMATION: Abu

<400> SEQUENCE: 74

Glu Lys Ala Arg His Gly Ser Cys Asn Tyr Val Phe Pro Ala
1               5                   10

<210> SEQ ID NO 75
<211> LENGTH: 14
<212> TYPE: PRT
<213> ORGANISM: Raphanus sativus
<220> FEATURE:
<221> NAME/KEY: MOD_RES
<222> LOCATION: 7
<223> OTHER INFORMATION: Abu

<400> SEQUENCE: 75

Lys Ala Arg His Gly Ser Cys Asn Tyr Val Phe Pro Ala His
1               5                   10

<210> SEQ ID NO 76
<211> LENGTH: 14
<212> TYPE: PRT
<213> ORGANISM: Raphanus sativus
<220> FEATURE:
<221> NAME/KEY: MOD_RES
<222> LOCATION: 6
<223> OTHER INFORMATION: Abu

<400> SEQUENCE: 76

```
Ala Arg His Gly Ser Cys Asn Tyr Val Phe Pro Ala His Lys
 1               5                  10
```

<210> SEQ ID NO 77
<211> LENGTH: 14
<212> TYPE: PRT
<213> ORGANISM: Raphanus sativus
<220> FEATURE:
<221> NAME/KEY: MOD_RES
<222> LOCATION: 5
<223> OTHER INFORMATION: Abu
<221> NAME/KEY: MOD_RES
<222> LOCATION: 14
<223> OTHER INFORMATION: Abu

<400> SEQUENCE: 77

```
Arg His Gly Ser Cys Asn Tyr Val Phe Pro Ala His Lys Cys
 1               5                  10
```

<210> SEQ ID NO 78
<211> LENGTH: 14
<212> TYPE: PRT
<213> ORGANISM: Raphanus sativus
<220> FEATURE:
<221> NAME/KEY: MOD_RES
<222> LOCATION: 4
<223> OTHER INFORMATION: Abu
<221> NAME/KEY: MOD_RES
<222> LOCATION: 13
<223> OTHER INFORMATION: Abu

<400> SEQUENCE: 78

```
His Gly Ser Cys Asn Tyr Val Phe Pro Ala His Lys Cys Ile
 1               5                  10
```

<210> SEQ ID NO 79
<211> LENGTH: 14
<212> TYPE: PRT
<213> ORGANISM: Raphanus sativus
<220> FEATURE:
<221> NAME/KEY: MOD_RES
<222> LOCATION: 3
<223> OTHER INFORMATION: Abu
<221> NAME/KEY: MOD_RES
<222> LOCATION: 12
<223> OTHER INFORMATION: Abu
<221> NAME/KEY: MOD_RES
<222> LOCATION: 14
<223> OTHER INFORMATION: Abu

<400> SEQUENCE: 79

```
Gly Ser Cys Asn Tyr Val Phe Pro Ala His Lys Cys Ile Cys
 1               5                  10
```

<210> SEQ ID NO 80
<211> LENGTH: 14
<212> TYPE: PRT
<213> ORGANISM: Raphanus sativus
<220> FEATURE:
<221> NAME/KEY: MOD_RES
<222> LOCATION: 2
<223> OTHER INFORMATION: Abu
<221> NAME/KEY: MOD_RES
<222> LOCATION: 11
<223> OTHER INFORMATION: Abu
<221> NAME/KEY: MOD_RES
<222> LOCATION: 13
<223> OTHER INFORMATION: Abu

<400> SEQUENCE: 80

```
Ser Cys Asn Tyr Val Phe Pro Ala His Lys Cys Ile Cys Tyr
 1               5                  10
```

```
<210> SEQ ID NO 81
<211> LENGTH: 14
<212> TYPE: PRT
<213> ORGANISM: Raphanus sativus
<220> FEATURE:
<221> NAME/KEY: MOD_RES
<222> LOCATION: 1
<223> OTHER INFORMATION: Abu
<221> NAME/KEY: MOD_RES
<222> LOCATION: 10
<223> OTHER INFORMATION: Abu
<221> NAME/KEY: MOD_RES
<222> LOCATION: 12
<223> OTHER INFORMATION: Abu

<400> SEQUENCE: 81
```

```
Cys Asn Tyr Val Phe Pro Ala His Lys Cys Ile Cys Tyr Phe
 1               5                  10
```

```
<210> SEQ ID NO 82
<211> LENGTH: 15
<212> TYPE: PRT
<213> ORGANISM: Raphanus sativus
<220> FEATURE:
<221> NAME/KEY: MOD_RES
<222> LOCATION: 11
<223> OTHER INFORMATION: Abu

<400> SEQUENCE: 82
```

```
Ile Arg Leu Glu Lys Ala Arg His Gly Ser Cys Asn Tyr Val Phe
 1               5                  10                  15
```

```
<210> SEQ ID NO 83
<211> LENGTH: 15
<212> TYPE: PRT
<213> ORGANISM: Raphanus sativus
<220> FEATURE:
<221> NAME/KEY: MOD_RES
<222> LOCATION: 10
<223> OTHER INFORMATION: Abu

<400> SEQUENCE: 83
```

```
Arg Leu Glu Lys Ala Arg His Gly Ser Cys Asn Tyr Val Phe Pro
 1               5                  10                  15
```

```
<210> SEQ ID NO 84
<211> LENGTH: 15
<212> TYPE: PRT
<213> ORGANISM: Raphanus sativus
<220> FEATURE:
<221> NAME/KEY: MOD_RES
<222> LOCATION: 9
<223> OTHER INFORMATION: Abu

<400> SEQUENCE: 84
```

```
Leu Glu Lys Ala Arg His Gly Ser Cys Asn Tyr Val Phe Pro Ala
 1               5                  10                  15
```

```
<210> SEQ ID NO 85
<211> LENGTH: 15
<212> TYPE: PRT
<213> ORGANISM: Raphanus sativus
<220> FEATURE:
<221> NAME/KEY: MOD_RES
<222> LOCATION: 8
<223> OTHER INFORMATION: Abu
```

-continued

<400> SEQUENCE: 85

Glu Lys Ala Arg His Gly Ser Cys Asn Tyr Val Phe Pro Ala His
1               5                   10                  15

<210> SEQ ID NO 86
<211> LENGTH: 15
<212> TYPE: PRT
<213> ORGANISM: Raphanus sativus
<220> FEATURE:
<221> NAME/KEY: MOD_RES
<222> LOCATION: 7
<223> OTHER INFORMATION: Abu

<400> SEQUENCE: 86

Lys Ala Arg His Gly Ser Cys Asn Tyr Val Phe Pro Ala His Lys
1               5                   10                  15

<210> SEQ ID NO 87
<211> LENGTH: 15
<212> TYPE: PRT
<213> ORGANISM: Raphanus sativus
<220> FEATURE:
<221> NAME/KEY: MOD_RES
<222> LOCATION: 6
<223> OTHER INFORMATION: Abu
<221> NAME/KEY: MOD_RES
<222> LOCATION: 15
<223> OTHER INFORMATION: Abu

<400> SEQUENCE: 87

Ala Arg His Gly Ser Cys Asn Tyr Val Phe Pro Ala His Lys Cys
1               5                   10                  15

<210> SEQ ID NO 88
<211> LENGTH: 15
<212> TYPE: PRT
<213> ORGANISM: Raphanus sativus
<220> FEATURE:
<221> NAME/KEY: MOD_RES
<222> LOCATION: 5
<223> OTHER INFORMATION: Abu
<221> NAME/KEY: MOD_RES
<222> LOCATION: 14
<223> OTHER INFORMATION: Abu

<400> SEQUENCE: 88

Arg His Gly Ser Cys Asn Tyr Val Phe Pro Ala His Lys Cys Ile
1               5                   10                  15

<210> SEQ ID NO 89
<211> LENGTH: 15
<212> TYPE: PRT
<213> ORGANISM: Raphanus sativus
<220> FEATURE:
<221> NAME/KEY: MOD_RES
<222> LOCATION: 4
<223> OTHER INFORMATION: Abu
<221> NAME/KEY: MOD_RES
<222> LOCATION: 13
<223> OTHER INFORMATION: Abu
<221> NAME/KEY: MOD_RES
<222> LOCATION: 15
<223> OTHER INFORMATION: Abu

<400> SEQUENCE: 89

His Gly Ser Cys Asn Tyr Val Phe Pro Ala His Lys Cys Ile Cys
1               5                   10                  15

<210> SEQ ID NO 90

```
<211> LENGTH: 15
<212> TYPE: PRT
<213> ORGANISM: Raphanus sativus
<220> FEATURE:
<221> NAME/KEY: MOD_RES
<222> LOCATION: 3
<223> OTHER INFORMATION: Abu
<221> NAME/KEY: MOD_RES
<222> LOCATION: 12
<223> OTHER INFORMATION: Abu
<221> NAME/KEY: MOD_RES
<222> LOCATION: 14
<223> OTHER INFORMATION: Abu

<400> SEQUENCE: 90

Gly Ser Cys Asn Tyr Val Phe Pro Ala His Lys Cys Ile Cys Tyr
 1               5                  10                  15

<210> SEQ ID NO 91
<211> LENGTH: 15
<212> TYPE: PRT
<213> ORGANISM: Raphanus sativus
<220> FEATURE:
<221> NAME/KEY: MOD_RES
<222> LOCATION: 2
<223> OTHER INFORMATION: Abu
<221> NAME/KEY: MOD_RES
<222> LOCATION: 11
<223> OTHER INFORMATION: Abu
<221> NAME/KEY: MOD_RES
<222> LOCATION: 13
<223> OTHER INFORMATION: Abu

<400> SEQUENCE: 91

Ser Cys Asn Tyr Val Phe Pro Ala His Lys Cys Ile Cys Tyr Phe
 1               5                  10                  15

<210> SEQ ID NO 92
<211> LENGTH: 16
<212> TYPE: PRT
<213> ORGANISM: Raphanus sativus
<220> FEATURE:
<221> NAME/KEY: MOD_RES
<222> LOCATION: 11
<223> OTHER INFORMATION: Abu

<400> SEQUENCE: 92

Ile Arg Leu Glu Lys Ala Arg His Gly Ser Cys Asn Tyr Val Phe Pro
 1               5                  10                  15

<210> SEQ ID NO 93
<211> LENGTH: 16
<212> TYPE: PRT
<213> ORGANISM: Raphanus sativus
<220> FEATURE:
<221> NAME/KEY: MOD_RES
<222> LOCATION: 10
<223> OTHER INFORMATION: Abu

<400> SEQUENCE: 93

Arg Leu Glu Lys Ala Arg His Gly Ser Cys Asn Tyr Val Phe Pro Ala
 1               5                  10                  15

<210> SEQ ID NO 94
<211> LENGTH: 16
<212> TYPE: PRT
<213> ORGANISM: Raphanus sativus
<220> FEATURE:
<221> NAME/KEY: MOD_RES
<222> LOCATION: 9
<223> OTHER INFORMATION: Abu
```

```
<400> SEQUENCE: 94

Leu Glu Lys Ala Arg His Gly Ser Cys Asn Tyr Val Phe Pro Ala His
 1               5                  10                  15

<210> SEQ ID NO 95
<211> LENGTH: 16
<212> TYPE: PRT
<213> ORGANISM: Raphanus sativus
<220> FEATURE:
<221> NAME/KEY: MOD_RES
<222> LOCATION: 8
<223> OTHER INFORMATION: Abu

<400> SEQUENCE: 95

Glu Lys Ala Arg His Gly Ser Cys Asn Tyr Val Phe Pro Ala His Lys
 1               5                  10                  15

<210> SEQ ID NO 96
<211> LENGTH: 16
<212> TYPE: PRT
<213> ORGANISM: Raphanus sativus
<220> FEATURE:
<221> NAME/KEY: MOD_RES
<222> LOCATION: 7
<223> OTHER INFORMATION: Abu
<221> NAME/KEY: MOD_RES
<222> LOCATION: 16
<223> OTHER INFORMATION: Abu

<400> SEQUENCE: 96

Lys Ala Arg His Gly Ser Cys Asn Tyr Val Phe Pro Ala His Lys Cys
 1               5                  10                  15

<210> SEQ ID NO 97
<211> LENGTH: 16
<212> TYPE: PRT
<213> ORGANISM: Raphanus sativus
<220> FEATURE:
<221> NAME/KEY: MOD_RES
<222> LOCATION: 6
<223> OTHER INFORMATION: Abu
<221> NAME/KEY: MOD_RES
<222> LOCATION: 15
<223> OTHER INFORMATION: Abu

<400> SEQUENCE: 97

Ala Arg His Gly Ser Cys Asn Tyr Val Phe Pro Ala His Lys Cys Ile
 1               5                  10                  15

<210> SEQ ID NO 98
<211> LENGTH: 16
<212> TYPE: PRT
<213> ORGANISM: Raphanus sativus
<220> FEATURE:
<221> NAME/KEY: MOD_RES
<222> LOCATION: 5
<223> OTHER INFORMATION: Abu
<221> NAME/KEY: MOD_RES
<222> LOCATION: 14
<223> OTHER INFORMATION: Abu
<221> NAME/KEY: MOD_RES
<222> LOCATION: 16
<223> OTHER INFORMATION: Abu

<400> SEQUENCE: 98

Arg His Gly Ser Cys Asn Tyr Val Phe Pro Ala His Lys Cys Ile Cys
 1               5                  10                  15
```

```
<210> SEQ ID NO 99
<211> LENGTH: 16
<212> TYPE: PRT
<213> ORGANISM: Raphanus sativus
<220> FEATURE:
<221> NAME/KEY: MOD_RES
<222> LOCATION: 4
<223> OTHER INFORMATION: Abu
<221> NAME/KEY: MOD_RES
<222> LOCATION: 13
<223> OTHER INFORMATION: Abu
<221> NAME/KEY: MOD_RES
<222> LOCATION: 15
<223> OTHER INFORMATION: Abu

<400> SEQUENCE: 99

His Gly Ser Cys Asn Tyr Val Phe Pro Ala His Lys Cys Ile Cys Tyr
1               5                   10                  15

<210> SEQ ID NO 100
<211> LENGTH: 16
<212> TYPE: PRT
<213> ORGANISM: Raphanus sativus
<220> FEATURE:
<221> NAME/KEY: MOD_RES
<222> LOCATION: 3
<223> OTHER INFORMATION: Abu
<221> NAME/KEY: MOD_RES
<222> LOCATION: 12
<223> OTHER INFORMATION: Abu
<221> NAME/KEY: MOD_RES
<222> LOCATION: 14
<223> OTHER INFORMATION: Abu

<400> SEQUENCE: 100

Gly Ser Cys Asn Tyr Val Phe Pro Ala His Lys Cys Ile Cys Tyr Phe
1               5                   10                  15

<210> SEQ ID NO 101
<211> LENGTH: 17
<212> TYPE: PRT
<213> ORGANISM: Raphanus sativus
<220> FEATURE:
<221> NAME/KEY: MOD_RES
<222> LOCATION: 11
<223> OTHER INFORMATION: Abu

<400> SEQUENCE: 101

Ile Arg Leu Glu Lys Ala Arg His Gly Ser Cys Asn Tyr Val Phe Pro
1               5                   10                  15

Ala

<210> SEQ ID NO 102
<211> LENGTH: 17
<212> TYPE: PRT
<213> ORGANISM: Raphanus sativus
<220> FEATURE:
<221> NAME/KEY: MOD_RES
<222> LOCATION: 10
<223> OTHER INFORMATION: Abu

<400> SEQUENCE: 102

Arg Leu Glu Lys Ala Arg His Gly Ser Cys Asn Tyr Val Phe Pro Ala
1               5                   10                  15

His

<210> SEQ ID NO 103
<211> LENGTH: 17
<212> TYPE: PRT
```

```
<213> ORGANISM: Raphanus sativus
<220> FEATURE:
<221> NAME/KEY: MOD_RES
<222> LOCATION: 9
<223> OTHER INFORMATION: Abu

<400> SEQUENCE: 103

Leu Glu Lys Ala Arg His Gly Ser Cys Asn Tyr Val Phe Pro Ala His
 1               5                  10                  15

Lys

<210> SEQ ID NO 104
<211> LENGTH: 17
<212> TYPE: PRT
<213> ORGANISM: Raphanus sativus
<220> FEATURE:
<221> NAME/KEY: MOD_RES
<222> LOCATION: 8
<223> OTHER INFORMATION: Abu
<221> NAME/KEY: MOD_RES
<222> LOCATION: 17
<223> OTHER INFORMATION: Abu

<400> SEQUENCE: 104

Glu Lys Ala Arg His Gly Ser Cys Asn Tyr Val Phe Pro Ala His Lys
 1               5                  10                  15

Cys

<210> SEQ ID NO 105
<211> LENGTH: 17
<212> TYPE: PRT
<213> ORGANISM: Raphanus sativus
<220> FEATURE:
<221> NAME/KEY: MOD_RES
<222> LOCATION: 7
<223> OTHER INFORMATION: Abu
<221> NAME/KEY: MOD_RES
<222> LOCATION: 16
<223> OTHER INFORMATION: Abu

<400> SEQUENCE: 105

Lys Ala Arg His Gly Ser Cys Asn Tyr Val Phe Pro Ala His Lys Cys
 1               5                  10                  15

Ile

<210> SEQ ID NO 106
<211> LENGTH: 17
<212> TYPE: PRT
<213> ORGANISM: Raphanus sativus
<220> FEATURE:
<221> NAME/KEY: MOD_RES
<222> LOCATION: 6
<223> OTHER INFORMATION: Abu
<221> NAME/KEY: MOD_RES
<222> LOCATION: 15
<223> OTHER INFORMATION: Abu
<221> NAME/KEY: MOD_RES
<222> LOCATION: 17
<223> OTHER INFORMATION: Abu

<400> SEQUENCE: 106

Ala Arg His Gly Ser Cys Asn Tyr Val Phe Pro Ala His Lys Cys Ile
 1               5                  10                  15

Cys

<210> SEQ ID NO 107
<211> LENGTH: 17
```

```
<212> TYPE: PRT
<213> ORGANISM: Raphanus sativus
<220> FEATURE:
<221> NAME/KEY: MOD_RES
<222> LOCATION: 5
<223> OTHER INFORMATION: Abu
<221> NAME/KEY: MOD_RES
<222> LOCATION: 14
<223> OTHER INFORMATION: Abu
<221> NAME/KEY: MOD_RES
<222> LOCATION: 16
<223> OTHER INFORMATION: Abu

<400> SEQUENCE: 107

Arg His Gly Ser Cys Asn Tyr Val Phe Pro Ala His Lys Cys Ile Cys
 1               5                  10                  15
Tyr

<210> SEQ ID NO 108
<211> LENGTH: 17
<212> TYPE: PRT
<213> ORGANISM: Raphanus sativus
<220> FEATURE:
<221> NAME/KEY: MOD_RES
<222> LOCATION: 4
<223> OTHER INFORMATION: Abu
<221> NAME/KEY: MOD_RES
<222> LOCATION: 13
<223> OTHER INFORMATION: Abu
<221> NAME/KEY: MOD_RES
<222> LOCATION: 15
<223> OTHER INFORMATION: Abu

<400> SEQUENCE: 108

His Gly Ser Cys Asn Tyr Val Phe Pro Ala His Lys Cys Ile Cys Tyr
 1               5                  10                  15
Phe

<210> SEQ ID NO 109
<211> LENGTH: 18
<212> TYPE: PRT
<213> ORGANISM: Raphanus sativus
<220> FEATURE:
<221> NAME/KEY: MOD_RES
<222> LOCATION: 11
<223> OTHER INFORMATION: Abu

<400> SEQUENCE: 109

Ile Arg Leu Glu Lys Ala Arg His Gly Ser Cys Asn Tyr Val Phe Pro
 1               5                  10                  15
Ala His

<210> SEQ ID NO 110
<211> LENGTH: 18
<212> TYPE: PRT
<213> ORGANISM: Raphanus sativus
<220> FEATURE:
<221> NAME/KEY: MOD_RES
<222> LOCATION: 10
<223> OTHER INFORMATION: Abu

<400> SEQUENCE: 110

Arg Leu Glu Lys Ala Arg His Gly Ser Cys Asn Tyr Val Phe Pro Ala
 1               5                  10                  15
His Lys

<210> SEQ ID NO 111
```

```
<211> LENGTH: 18
<212> TYPE: PRT
<213> ORGANISM: Raphanus sativus
<220> FEATURE:
<221> NAME/KEY: MOD_RES
<222> LOCATION: 9
<223> OTHER INFORMATION: Abu
<221> NAME/KEY: MOD_RES
<222> LOCATION: 18
<223> OTHER INFORMATION: Abu

<400> SEQUENCE: 111

Leu Glu Lys Ala Arg His Gly Ser Cys Asn Tyr Val Phe Pro Ala His
 1               5                  10                  15
Lys Cys

<210> SEQ ID NO 112
<211> LENGTH: 18
<212> TYPE: PRT
<213> ORGANISM: Raphanus sativus
<220> FEATURE:
<221> NAME/KEY: MOD_RES
<222> LOCATION: 8
<223> OTHER INFORMATION: Abu
<221> NAME/KEY: MOD_RES
<222> LOCATION: 17
<223> OTHER INFORMATION: Abu

<400> SEQUENCE: 112

Glu Lys Ala Arg His Gly Ser Cys Asn Tyr Val Phe Pro Ala His Lys
 1               5                  10                  15
Cys Ile

<210> SEQ ID NO 113
<211> LENGTH: 18
<212> TYPE: PRT
<213> ORGANISM: Raphanus sativus
<220> FEATURE:
<221> NAME/KEY: MOD_RES
<222> LOCATION: 7
<223> OTHER INFORMATION: Abu
<221> NAME/KEY: MOD_RES
<222> LOCATION: 16
<223> OTHER INFORMATION: Abu
<221> NAME/KEY: MOD_RES
<222> LOCATION: 18
<223> OTHER INFORMATION: Abu

<400> SEQUENCE: 113

Lys Ala Arg His Gly Ser Cys Asn Tyr Val Phe Pro Ala His Lys Cys
 1               5                  10                  15
Ile Cys

<210> SEQ ID NO 114
<211> LENGTH: 18
<212> TYPE: PRT
<213> ORGANISM: Raphanus sativus
<220> FEATURE:
<221> NAME/KEY: MOD_RES
<222> LOCATION: 6
<223> OTHER INFORMATION: Abu
<221> NAME/KEY: MOD_RES
<222> LOCATION: 15
<223> OTHER INFORMATION: Abu
<221> NAME/KEY: MOD_RES
<222> LOCATION: 17
<223> OTHER INFORMATION: Abu

<400> SEQUENCE: 114
```

Ala Arg His Gly Ser Cys Asn Tyr Val Phe Pro Ala His Lys Cys Ile
1               5                   10                  15

Cys Tyr

<210> SEQ ID NO 115
<211> LENGTH: 18
<212> TYPE: PRT
<213> ORGANISM: Raphanus sativus
<220> FEATURE:
<221> NAME/KEY: MOD_RES
<222> LOCATION: 5
<223> OTHER INFORMATION: Abu
<221> NAME/KEY: MOD_RES
<222> LOCATION: 14
<223> OTHER INFORMATION: Abu
<221> NAME/KEY: MOD_RES
<222> LOCATION: 16
<223> OTHER INFORMATION: Abu

<400> SEQUENCE: 115

Arg His Gly Ser Cys Asn Tyr Val Phe Pro Ala His Lys Cys Ile Cys
1               5                   10                  15

Tyr Phe

<210> SEQ ID NO 116
<211> LENGTH: 19
<212> TYPE: PRT
<213> ORGANISM: Raphanus sativus
<220> FEATURE:
<221> NAME/KEY: MOD_RES
<222> LOCATION: 11
<223> OTHER INFORMATION: Abu

<400> SEQUENCE: 116

Ile Arg Leu Glu Lys Ala Arg His Gly Ser Cys Asn Tyr Val Phe Pro
1               5                   10                  15

Ala His Lys

<210> SEQ ID NO 117
<211> LENGTH: 19
<212> TYPE: PRT
<213> ORGANISM: Raphanus sativus
<220> FEATURE:
<221> NAME/KEY: MOD_RES
<222> LOCATION: 10
<223> OTHER INFORMATION: Abu
<221> NAME/KEY: MOD_RES
<222> LOCATION: 19
<223> OTHER INFORMATION: Abu

<400> SEQUENCE: 117

Arg Leu Glu Lys Ala Arg His Gly Ser Cys Asn Tyr Val Phe Pro Ala
1               5                   10                  15

His Lys Cys

<210> SEQ ID NO 118
<211> LENGTH: 19
<212> TYPE: PRT
<213> ORGANISM: Raphanus sativus
<220> FEATURE:
<221> NAME/KEY: MOD_RES
<222> LOCATION: 9
<223> OTHER INFORMATION: Abu
<221> NAME/KEY: MOD_RES
<222> LOCATION: 18
<223> OTHER INFORMATION: Abu

<400> SEQUENCE: 118

Leu Glu Lys Ala Arg His Gly Ser Cys Asn Tyr Val Phe Pro Ala His
 1               5                  10                  15

Lys Cys Ile

<210> SEQ ID NO 119
<211> LENGTH: 19
<212> TYPE: PRT
<213> ORGANISM: Raphanus sativus
<220> FEATURE:
<221> NAME/KEY: MOD_RES
<222> LOCATION: 8
<223> OTHER INFORMATION: Abu
<221> NAME/KEY: MOD_RES
<222> LOCATION: 17
<223> OTHER INFORMATION: Abu
<221> NAME/KEY: MOD_RES
<222> LOCATION: 19
<223> OTHER INFORMATION: Abu

<400> SEQUENCE: 119

Glu Lys Ala Arg His Gly Ser Cys Asn Tyr Val Phe Pro Ala His Lys
 1               5                  10                  15

Cys Ile Cys

<210> SEQ ID NO 120
<211> LENGTH: 19
<212> TYPE: PRT
<213> ORGANISM: Raphanus sativus
<220> FEATURE:
<221> NAME/KEY: MOD_RES
<222> LOCATION: 7
<223> OTHER INFORMATION: Abu
<221> NAME/KEY: MOD_RES
<222> LOCATION: 16
<223> OTHER INFORMATION: Abu
<221> NAME/KEY: MOD_RES
<222> LOCATION: 18
<223> OTHER INFORMATION: Abu

<400> SEQUENCE: 120

Lys Ala Arg His Gly Ser Cys Asn Tyr Val Phe Pro Ala His Lys Cys
 1               5                  10                  15

Ile Cys Tyr

<210> SEQ ID NO 121
<211> LENGTH: 19
<212> TYPE: PRT
<213> ORGANISM: Raphanus sativus
<220> FEATURE:
<221> NAME/KEY: MOD_RES
<222> LOCATION: 6
<223> OTHER INFORMATION: Abu
<221> NAME/KEY: MOD_RES
<222> LOCATION: 15
<223> OTHER INFORMATION: Abu
<221> NAME/KEY: MOD_RES
<222> LOCATION: 17
<223> OTHER INFORMATION: Abu

<400> SEQUENCE: 121

Ala Arg His Gly Ser Cys Asn Tyr Val Phe Pro Ala His Lys Cys Ile
 1               5                  10                  15

Cys Tyr Phe

<210> SEQ ID NO 122
<211> LENGTH: 20
<212> TYPE: PRT

<213> ORGANISM: Raphanus sativus
<220> FEATURE:
<221> NAME/KEY: MOD_RES
<222> LOCATION: 11
<223> OTHER INFORMATION: Abu
<221> NAME/KEY: MOD_RES
<222> LOCATION: 20
<223> OTHER INFORMATION: Abu

<400> SEQUENCE: 122

Ile Arg Leu Glu Lys Ala Arg His Gly Ser Cys Asn Tyr Val Phe Pro
 1               5                  10                  15

Ala His Lys Cys
            20

<210> SEQ ID NO 123
<211> LENGTH: 20
<212> TYPE: PRT
<213> ORGANISM: Raphanus sativus
<220> FEATURE:
<221> NAME/KEY: MOD_RES
<222> LOCATION: 10
<223> OTHER INFORMATION: Abu
<221> NAME/KEY: MOD_RES
<222> LOCATION: 19
<223> OTHER INFORMATION: Abu

<400> SEQUENCE: 123

Arg Leu Glu Lys Ala Arg His Gly Ser Cys Asn Tyr Val Phe Pro Ala
 1               5                  10                  15

His Lys Cys Ile
            20

<210> SEQ ID NO 124
<211> LENGTH: 20
<212> TYPE: PRT
<213> ORGANISM: Raphanus sativus
<220> FEATURE:
<221> NAME/KEY: MOD_RES
<222> LOCATION: 9
<223> OTHER INFORMATION: Abu
<221> NAME/KEY: MOD_RES
<222> LOCATION: 18
<223> OTHER INFORMATION: Abu
<221> NAME/KEY: MOD_RES
<222> LOCATION: 20
<223> OTHER INFORMATION: Abu

<400> SEQUENCE: 124

Leu Glu Lys Ala Arg His Gly Ser Cys Asn Tyr Val Phe Pro Ala His
 1               5                  10                  15

Lys Cys Ile Cys
            20

<210> SEQ ID NO 125
<211> LENGTH: 20
<212> TYPE: PRT
<213> ORGANISM: Raphanus sativus
<220> FEATURE:
<221> NAME/KEY: MOD_RES
<222> LOCATION: 8
<223> OTHER INFORMATION: Abu
<221> NAME/KEY: MOD_RES
<222> LOCATION: 17
<223> OTHER INFORMATION: Abu
<221> NAME/KEY: MOD_RES
<222> LOCATION: 19
<223> OTHER INFORMATION: Abu

<400> SEQUENCE: 125

Glu Lys Ala Arg His Gly Ser Cys Asn Tyr Val Phe Pro Ala His Lys
1               5                   10                  15

Cys Ile Cys Tyr
            20

<210> SEQ ID NO 126
<211> LENGTH: 20
<212> TYPE: PRT
<213> ORGANISM: Raphanus sativus
<220> FEATURE:
<221> NAME/KEY: MOD_RES
<222> LOCATION: 7
<223> OTHER INFORMATION: Abu
<221> NAME/KEY: MOD_RES
<222> LOCATION: 16
<223> OTHER INFORMATION: Abu
<221> NAME/KEY: MOD_RES
<222> LOCATION: 18
<223> OTHER INFORMATION: Abu

<400> SEQUENCE: 126

Lys Ala Arg His Gly Ser Cys Asn Tyr Val Phe Pro Ala His Lys Cys
1               5                   10                  15

Ile Cys Tyr Phe
            20

<210> SEQ ID NO 127
<211> LENGTH: 19
<212> TYPE: PRT
<213> ORGANISM: Aesculus hippocastanum

<400> SEQUENCE: 127

Ala Ser His Gly Ala Cys His Lys Arg Glu Asn His Trp Lys Cys Phe
1               5                   10                  15

Cys Tyr Phe

<210> SEQ ID NO 128
<211> LENGTH: 19
<212> TYPE: PRT
<213> ORGANISM: Dahlia merckii

<400> SEQUENCE: 128

Ala Ala His Gly Ala Cys His Val Arg Asn Gly Lys His Met Cys Phe
1               5                   10                  15

Cys Tyr Phe

<210> SEQ ID NO 129
<211> LENGTH: 6
<212> TYPE: PRT
<213> ORGANISM: Raphanus sativus

<400> SEQUENCE: 129

Cys Ile Cys Tyr Phe Pro
1               5

<210> SEQ ID NO 130
<211> LENGTH: 6
<212> TYPE: PRT
<213> ORGANISM: Raphanus sativus

<400> SEQUENCE: 130

Ile Cys Tyr Phe Pro Cys
1               5

```
<210> SEQ ID NO 131
<211> LENGTH: 12
<212> TYPE: PRT
<213> ORGANISM: Raphanus sativus

<400> SEQUENCE: 131

Val Phe Pro Ala His Lys Cys Ile Cys Tyr Phe Pro
 1               5                  10

<210> SEQ ID NO 132
<211> LENGTH: 12
<212> TYPE: PRT
<213> ORGANISM: Raphanus sativus

<400> SEQUENCE: 132

Phe Pro Ala His Lys Cys Ile Cys Tyr Phe Pro Cys
 1               5                  10

<210> SEQ ID NO 133
<211> LENGTH: 6
<212> TYPE: PRT
<213> ORGANISM: Raphanus sativus

<400> SEQUENCE: 133

Gln Lys Leu Cys Gln Arg
 1               5

<210> SEQ ID NO 134
<211> LENGTH: 6
<212> TYPE: PRT
<213> ORGANISM: Raphanus sativus

<400> SEQUENCE: 134

Lys Leu Cys Gln Arg Pro
 1               5

<210> SEQ ID NO 135
<211> LENGTH: 6
<212> TYPE: PRT
<213> ORGANISM: Raphanus sativus

<400> SEQUENCE: 135

Leu Cys Gln Arg Pro Ser
 1               5

<210> SEQ ID NO 136
<211> LENGTH: 9
<212> TYPE: PRT
<213> ORGANISM: Raphanus sativus

<400> SEQUENCE: 136

Gln Lys Leu Cys Gln Arg Pro Ser Gly
 1               5

<210> SEQ ID NO 137
<211> LENGTH: 9
<212> TYPE: PRT
<213> ORGANISM: Raphanus sativus

<400> SEQUENCE: 137

Lys Leu Cys Gln Arg Pro Ser Gly Thr
 1               5

<210> SEQ ID NO 138
```

```
<211> LENGTH: 9
<212> TYPE: PRT
<213> ORGANISM: Raphanus sativus

<400> SEQUENCE: 138

Leu Cys Gln Arg Pro Ser Gly Thr Trp
 1               5

<210> SEQ ID NO 139
<211> LENGTH: 12
<212> TYPE: PRT
<213> ORGANISM: Raphanus sativus

<400> SEQUENCE: 139

Gln Lys Leu Cys Gln Arg Pro Ser Gly Thr Trp Ser
 1               5                  10

<210> SEQ ID NO 140
<211> LENGTH: 12
<212> TYPE: PRT
<213> ORGANISM: Raphanus sativus

<400> SEQUENCE: 140

Lys Leu Cys Gln Arg Pro Ser Gly Thr Trp Ser Gly
 1               5                  10

<210> SEQ ID NO 141
<211> LENGTH: 12
<212> TYPE: PRT
<213> ORGANISM: Raphanus sativus

<400> SEQUENCE: 141

Leu Cys Gln Arg Pro Ser Gly Thr Trp Ser Gly Val
 1               5                  10
```